United States Patent [19]
Baga et al.

[11] Patent Number: 5,866,793
[45] Date of Patent: Feb. 2, 1999

[54] PROMOTER FOR EXPRESSING FOREIGN GENES IN MONOCOTYLEDONOUS PLANTS

[75] Inventors: Monica Baga; Ravindra N. Chibbar; Kutty K. Kartha, all of Saskatoon, Canada

[73] Assignee: National Research Council of Canada, Ottawa, Canada

[21] Appl. No.: 773,251

[22] Filed: Dec. 23, 1996

[30] Foreign Application Priority Data

Jun. 3, 1996 [CA] Canada ................................ 2178016

[51] Int. Cl.$^6$ .............................. C12N 5/00; C12N 15/00; A01H 1/04; C07H 21/04
[52] U.S. Cl. .................... 800/205; 536/24.1; 435/172.3; 435/320.1; 435/419; 935/6; 935/35; 935/64
[58] Field of Search .......................... 800/205; 536/24.1; 435/172.3, 320.1, 419; 935/6, 35, 64

[56] References Cited

U.S. PATENT DOCUMENTS

| | | | |
|---|---|---|---|
| 4,525,496 | 6/1985 | Adaway et al. | 523/337 |
| 5,139,954 | 8/1992 | Litts et al. | 435/320.1 |
| 5,290,924 | 3/1994 | Last et al. | 536/24.1 |
| 5,405,765 | 4/1995 | Vasil et al. | 435/172.3 |

FOREIGN PATENT DOCUMENTS

| | | |
|---|---|---|
| WO 91/09948 | 7/1991 | WIPO . |
| WO 93/04178 | 4/1993 | WIPO . |

OTHER PUBLICATIONS

Båga M., Chibbar R.N. and Kartha K.K. (1995). Molecular cloning and expression analysis of peroxidase genes from wheat. Plant Mol. Biol. 29: 647–662.

Chibbar, R.N., Kartha, K.K., Datla, R.S.S., Leung, N., Caswell, K., Mallard, C. and Steinhauer, L. (1993). The effect of different promoter–sequences of gus reporter gene in cultured barley (*Hordeum vulgare* L.) cells. Plant Cell Reports 12: 506–509.

McElroy, D., Zhang, W., Cao, J. and Wu, R. (1990). Isolation of an efficient actin promoter for use in rice transformation. Plant Cell 2: 163–171.

Nehra, N.S., Chibbar, R.N., Leung, N., Caswell, K., Mallard, C., Steinhauer, L., Båga, M. and Kartha, K.K. (1994). Self–fertile transgenic wheat plants regenerated from isolated scutellar tissues following microprojectile bombardment with two distinct gene constructs. The Plant J. 5(2): 285–297.

MK Morell et al (1977) Plant Physiology 113:201–208.

*Primary Examiner*—Bruce R. Campbell

[57] ABSTRACT

A DNA fragment for directing the expression of foreign or endogenous genes or RNA in cells of monocot plants. The fragment comprises a sequence corresponding to a first part of a putative type I starch branching enzyme gene (wbeI) present in wheat and a 5'-region upstream of the gene, or a part of the sequence that is effective for increasing the expression of the foreign or endogenous gene in the plant cells. The indicated sequence contains two promoter regions, P1 and P2. A DNA fragment effective to increase expression comprises at least one of the promoter regions, or an effective part. The fragment can be obtained from a genomic library of wheat and can be fused to suitable genes and markers and inserted into suitable vectors for expression in transgenic monocot plants.

24 Claims, 8 Drawing Sheets

```
      SalI,AccI
    1 GTCGACGACCCGATCGACGTCCTGATGCGGCTCTCCACCCTGAAGAGCGCAACCAGGAGCGCATCAGTCGGAGAGTTCTGCCCTGCAACCATCGATGAGA
  101 AGGAGTCGCGGAGCTTGCCTCCACCTCCCAAAAATGTCACTCAACTAAATGTCTCGGAGGAGGGGCTAGAGGACGTCGAGCAATAGTACAACAATAGAACAT
  201 AGGAATGTCGAATAGCGACATCCAAAAATGTCACTCAACTAAATGTCCTTGAACGACATTGAAGTCGCAAAAATGTAATACAACAGCTTTGCCAGTAATATAAGTTATC
  301 ATGTTTGATGATGGTTTGAGCTGGTTGGTTGGTTCAACTAAATGTACCTTAACTTCACACAGTGCACAATCGCCACAGTCTACTTGACCGAAATATCTACTAGAGTTGCTCTAAGGCCGCT
  401 AATATGGAGGCGCATATAGACTACGTGGTTGTGCACAATCGCCACAGTCTGTGCAGGGTGTCCATGTAGTTTTTTTAACATAGTGACACTCATATACACACAGTCCTTCTAACCATCC
  501 TTTTGCGTCTTCCACTTGTCGTGCAGTCCCGTATCCGTGAGCACTAGAAAGGCGAGCGGGACTTGAACCCTGGTAGGGAGACCACAGTCCTTCTAACCATCC
  601 TGAATGCACATACGCACACCGTATCCGTGAGCACTAGAAAGGCGAGCGGGACTTGAACCCTGGTAGGGAGACCACAGTCCTTCTAACCATCC
  701 AACCATTGGTTGATTCGCGGGAGCGATGGTAGTTGGACTAGTTCCATCCTTTCGAATTTCATCCTTTCTCTCTCTGGTTGTTCCAGATTTATATATCC
  801 TTTTTCATTCCCCTTTTTCTTCTTGTTTCTTTTCTCTGGAATTTCATCCTTTCGAATTTCATCCTTTCTCTCTCTGGAAATGCACACAAAACATAGAAAGTGTAAACACTA
  901 ACGTGAGAAGTATGTTTACACGTATAAATAATTAATCGAAACATACCAATATGGATTATAGTTCTGAATATAGATACGACCAATGCAACCACTTCAA
 1001 ATTTTGAACGCCCGATCTTATTTTTGAGGAAGTATATGATAAAACTCCGATCTAGCCCAACCACATGCTATAATCTTGTACCATATGAAAACCACGT
 1101 CTGCTATTTTGGCGGTTGCCTCAAAACAAAAGTAATGTTATCCGTTTCCAACTCAAAGAGAGTCAGGTAGCGTGAAGCTCCGAGGCTGAGATGGG
                                      AccI
 1201 GACGAGCATGGCGCCCCCTAGAGAGACCTCGCCGTAGACGGGGACATTGCGGTTGCAGTGCGGTTGCGAGATGCGTGAGACAACACGTT
 1301 AGCAAAGTAGGGAGAGGTAGAAGAATCTCGTTGGTTTCCACGCGACAAGTCCAACAGCCATAGGCGTCTCACATGCGTCTCCTTCTAGTCTTCGCAAAAA
 1401 AGGCCCTACAAAATCTCGTTGGTTTCCACGCGACAAGTCCAACAGCCATAGGCGTCTCACATGCGTCTCCTTCTAGTCTTCGCAAAAGCAG
 1501 GTAATTATTTTGCCGGACAATGCAAGGAGTGATATTTTATAGTTTTCCTTCGAATACTATAGTTTCCTTCTTCTTTTAGAACAAAGCATCTTACACTTTTTGGCAAAACCGA
 1601 TCCTTCCATAGTTTCTTTTGTGAAAGCAATGCCTTTTAGCAATGGGATGTTCCTTTTAGCGATGTTCCTTTTAGCGAGCAAAACATCTTACACTTTTTGGCAAAACCGA
 1701 CGACGAAGCTGGAAAAAAGAAGTGACGAAGCTGAAAGTGGCGAGACACGTGAGGCTTCCGTCCGGCCCAGCGGCCACGACCCCGGCCG
            ApaI
 1801 CCCGGCCACCCCACAGATCCGCTTCTCCCCCGTTCCCCCGCCCCCGTTGCTTCCAGTCGTTGCTTCCACTCCACTGTTCTCCTCCCTGTCCAAAGCGGCCAC
           AvaII                                                                         ApaI
 1901 GGACCGGGAAAAAATCACGGCTTTCCGTTGCCTTCCGGCGCCACACTCCTCCTCCCTCCGGCCGCTATAAAGCGCGCCGGGCCACGGGCCCGC
                                                                                           P1
 2001 GGACAATGGGATCCCCGTCCGGCCCATCGACGAAG ATG CTC TGC CTC ACC GCC TCC TCC TCG CCC TCG CCC TCT CTC             IA
              BamHI  ⇒                 M   L   C   L   T   A   S   S   S   P   S   P   S   L          (2037-2135)
             ApaI                                                          AvaII
 2085 CCG CCG CGC CCC TCC CGT CCC GCT GCT GAC CGG CCC GGA CCG GGG ATC TCG GTGAGTCACTCGGATCTTCATTCTTTTCTT        1a
       P   P   R   P   S   R   P   A   A   D   R   P   G   P   G   I   S                                 (2136-2231)
```

PROMOTER FOR EXPRESSING FOREIGN GENES IN MONOCOTYLEDONOUS PLANTS

BACKGROUND OF THE INVENTION

I. Field of the Invention

This invention relates to promoters used for expressing foreign genes introduced by genetic engineering techniques into cells of monocotyledonous (monocot) plants, especially cereals such as wheat, barley, maize, oat and rice.

II. Description of the Prior Art

Genetic engineering is a procedure in which desired genes are inserted and stably integrated into the host genome followed by regeneration and selection for transformed plants using tissue culture methods. The development of plant transformation techniques has opened up the possibility to introduce and express genes of diverse origins in plants and thereby created a powerful tool to supplement and complement traditional plant breeding.

Significant progress has recently been made in the genetic transformation of cereals, such as wheat (see, for example, Nehra, N. S., et al., "Wheat Transformation: Methods and Prospects," Plant Breeding Abstracts, 65(6):803–808, 1995, the disclosure of which is incorporated herein by reference). In particular, the inventors of the present invention have achieved the genetic transformation of wheat by biolistically delivering genes into isolated scutella, the starting explant for an enhanced regeneration system (Nehra, N. S., et al., "Self-fertile Transgenic Wheat Plants Regenerated From Isolated Scutellar Tissues Following Microprojectile Bombardment With Two Distinct Gene Constructs", The Plant J., 5(2):285–297, 1994, the disclosure of which is also incorporated herein by reference).

With the development of gene transfer techniques, the remaining limitation for commercial exploitation of genetic transformation technology in wheat and other monocot plants is the lack of efficient promoters that will direct foreign gene expression in transgenic wheat plants. Many of the most commonly used promoters employed to transform dicot plants show low activity in cereal cells. A rice actin promoter, which transiently expresses high activity of marker genes in cultured barley cells (Chibbar, R. N., et al., "The effect of Different Promoter-Sequences on Transient Expression of GUS Reporter Gene in Cultured Barley Hordeum vulgare L. cells", Plant Cell Reports, 12:506–509, 1993), has been successfully used in the production of transgenic wheat. Moreover, a promoter comprising the 5'-region of a rice RAc1 gene for use in rice is disclosed in PCT patent publication WO 91/09948 filed in the name of Cornell Research Foundation and published on Jul. 11, 1991; and a nucleic acid promoter fragment comprising the 5' flanking promoter region of the Em structural gene in wheat is disclosed in U.S. Pat. No. 5,139,954 issued on Aug. 18, 1992.

However, there is a need for more effective promoters for use in cereal plants, especially wheat, barley, maize, oat and rice.

SUMMARY OF THE INVENTION

An object of the present invention is to provide a DNA fragment that can be fused to desired genes to act as a promoter for expression and/or enhancing the expression of such genes in monocot plant cells.

Another object of the invention is to provide such a DNA fragment that is particularly effective in cereal plants, especially wheat, barley, maize, oat and rice.

Yet another object of the invention is to facilitate the expression of foreign genes in monocot plants, such as wheat, barley, maize, oat and rice.

A further object of the invention is to produce transgenic plants, such as wheat, barley, maize, oat and rice, in which foreign genes are expressed at desirable levels.

According to one aspect of the present invention, there is provided a DNA fragment for directing the expression of foreign or endogenous genes in cells of monocot plants. The fragment comprises a sequence corresponding to a first part of a putative type I starch branching enzyme gene (wbeI) present in wheat and a 5'-region upstream of the gene, or a part of the sequence that is effective for increasing the expression of the foreign or endogenous gene in the cells.

The type 1 starch branching enzyme genes of plants are denoted Sbe1 as recommended by the Commission on Plant Gene Nomenclature (CPGN) (B. Smith-White and J. Preiss; (1994) Suggested mnemonics for cloned DNA corresponding to enzymes involved in starch metabolism. Plant Molecular Biology Reporter, 12: S61–S71).

According to another aspect of the invention, there is provided a construct comprising a DNA fragment linked to a gene other than wbeI, said fragment being a sequence corresponding to a first part of a type I starch branching enzyme gene (wbeI) present in wheat and a 5'-region upstream of said gene, or a part of said sequence that is effective for increasing the expression of said foreign or endogenous gene in said cells.

According to yet another aspect of the invention, there is provided a method of producing transgenic monocot plants, which comprises introducing a vector comprising a foreign or endogenous gene and a DNA sequence corresponding to a first part of a type I starch branching enzyme gene (wbeI) present in wheat and a 5'-region upstream of said gene, or a part of said sequence that is effective to increase the expression of said foreign or endogenous gene, into a totipotent explant of a monocot plant to form a transformed explant, and culturing the transformed explant to form a mature transgenic monocot plant.

The invention also relates to vectors containing the fragments and constructs of the invention and transgenic plant cells modified by such vectors.

BRIEF DESCRIPTION OF THE DRAWINGS

FIG. 2 shows the nucleotide sequence [SEQ ID NO:1] of the wbeI 5' upstream region and first 1 kb of the transcribed region; the position numbers indicated on the left refer to the first SalI site upstream of wbeI (see construct pBE64:8-2 in FIG. 1); approximate start points of transcription from the P1 and P2 promoters are indicated by arrows; postulated translated sequences are in bold with deduced peptide sequences [SEQ ID NO:2 for P1 and SEQ ID NO:22 for P2] shown below; DNA sequences of postulated coding regions and introns are shown in the right panel;

DETAILED DESCRIPTION OF THE INVENTION AND THE PREFERRED EMBODIMENTS

I. General Discussion

Figure 1:
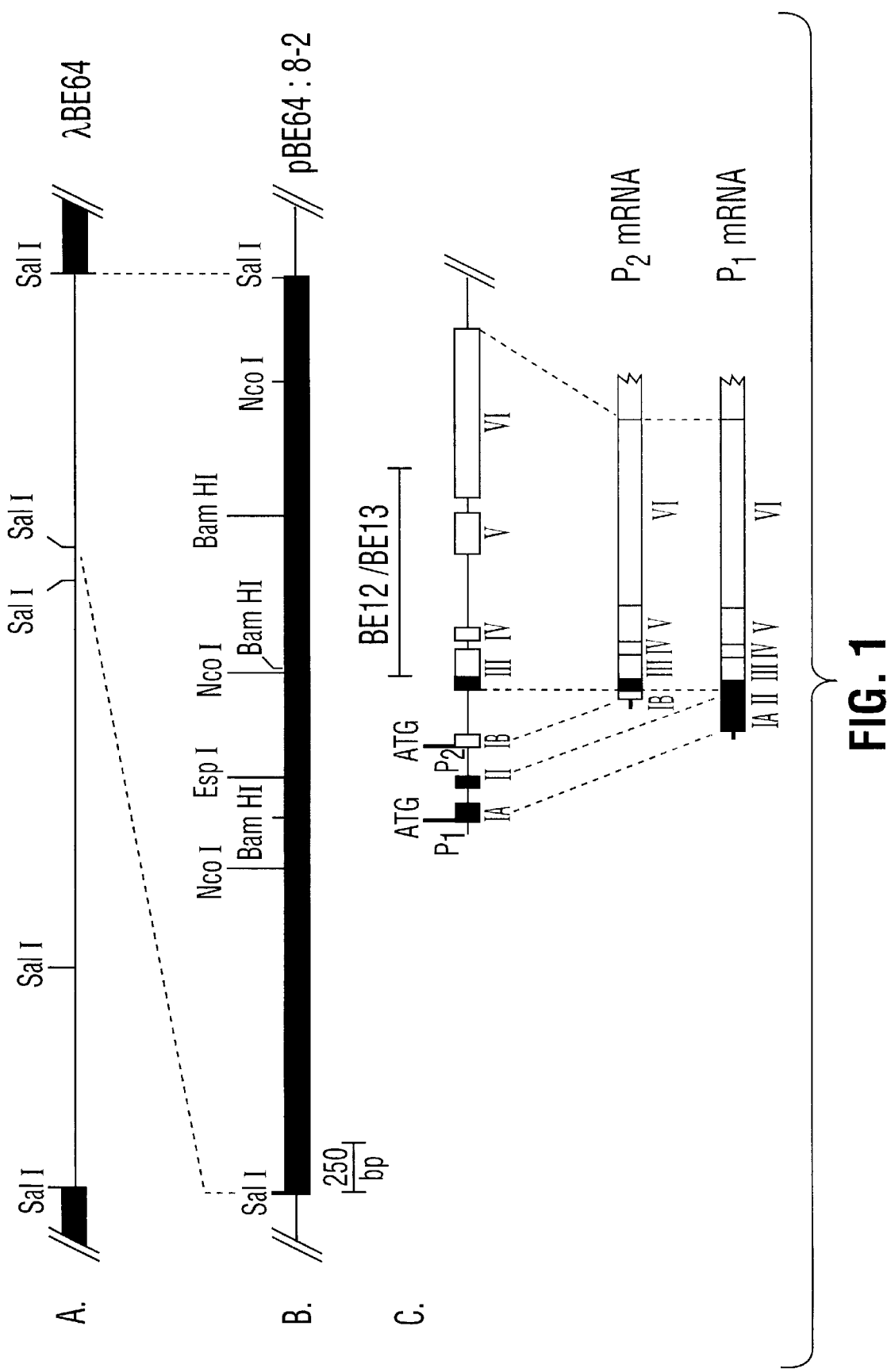
FIG. 1 has three interrelated parts, A, B and C; Part A is a schematic illustration of genomic DNA (thin line) carried by a λBE64 clone isolated from a genomic library of wheat; Part B is a restriction map of a 5.0 kb SalI fragment subcloned into a plasmid pUC19 to give a construct pBE64:8-2 carrying the first half of a putative type I starch branching enzyme gene (wbeI) and 2 kb of the 5' upstream region; and Part C, top line, shows a 1.25 kb wheat genomic DNA fragment amplified in PCR reactions with BE12 and BE13 primers [SEQ ID NOS: 9 and 10, respectively] and used as a probe in hybridization experiments, and the illustration below the top line of Part C indicates the proposed coding regions (boxes) and non-coding regions (lines) of wbeI with spliced forms of mRNA transcribed from the P2 and P1 promoters (filled parts of the boxes indicate putative sequences encoding a transit peptide)

As noted above, the present invention, at least in one of its aspects, relates to one or more DNA fragments that can be used as promoters for expressing endogenous or foreign genes in monocot plants, especially wheat, barley, maize, oat and rice.

The DNA sequences of the present invention include at least an effective part of a sequence present in vector λBE64 obtained from a genomic library of wheat. By the term "effective part" we mean a part of the indicated DNA sequence that, when fused to a particular gene and introduced into a monocot plant cell, causes expression of the gene at a level higher than is possible in the absence of such part of the indicated DNA sequence.

Figure 2:
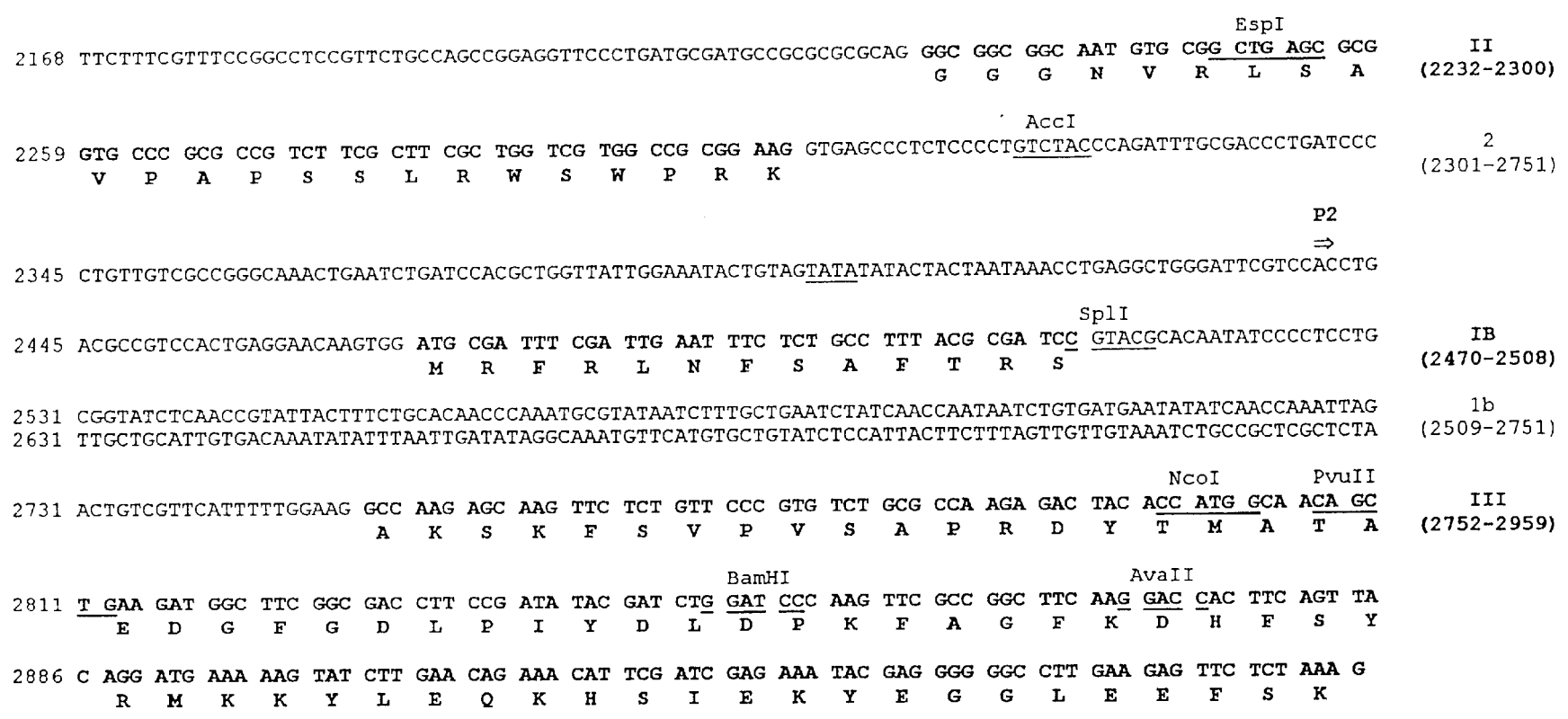

More specifically, the DNA fragments of the present invention comprise at least an effective part of the DNA sequence shown in FIG. 2 of the accompanying drawings [SEQ ID NO:1]. This sequence is believed to be derived from a gene encoding starch branching enzyme activity in wheat, but this has not been conclusively confirmed at the moment. This gene is referred to in the following disclosure as wbeI (putative wheat starch branching enzyme gene type I).

The DNA sequence shown in FIG. 2 [SEQ ID NO:1] is the 5' upstream region of wbeI and the first 1 kb of the transcribed region. The sequence has been found to contain two promoter regions, P1 and P2, the full sequences or effective parts of either or both of which may be present in the DNA fragments employed for the present invention to drive gene expression in monocot plants. It is believed that the P2 promoter is located upstream of position 2490 of the sequence of FIG. 2 [SEQ ID NO:1], and that the primary P2 transcript is spliced to fuse the coding sequence IB to the coding sequence III (see FIGS. 1 and 2). It is further believed that the TATA-rich sequence at position 2401 located 61 nucleotides upstream of an ATG codon constitutes the TATA-box for promoter P2 (FIG. 2). In FIG. 2, the approximate start points of transcription from the P1 and P2 promoters are indicated by arrows.

The entire DNA sequence shown in FIG. 2 [SEQ ID NO:1] may be used to drive gene expression according to the present invention, or a suitable fragment of this sequence containing at least a part of one or both of the promoter regions P1 and P2 may be used. It has been found that, in wheat, the use of a fragment of DNA containing only promoter P2 demonstrates a high level of expression activity, whereas the use of a fragment containing only promoter P1 demonstrates a lower (but still enhanced) level of activity. A fragment containing the P2 promoter is therefore useful when a high level of gene expression is required, whereas a fragment containing only the promoter P1 may be preferred when high levels of expression have negative effects on the resulting transgenic cells/plants. Fragments containing the sequences of both P1 and P2 have intermediate levels of expression.

In wheat, the most active DNA fragment comprises nucleotides 1997–2803 [SEQ ID NO:3] of the sequence of FIG. 2. One of the shortest functional fragments isolated to date comprises nucleotides 2251–2803 [SEQ ID NO:4] of the sequence of FIG. 2.

The indicated fragments of the present invention can be fused to foreign genes of diverse origins and incorporated into vectors designed for genetic transformation of plants and then used in standard genetic engineering techniques. For example, an isolated fragment according to the present invention may be linked to a target gene that encodes a functional protein or RNA. The gene linked to the promoter fragment may be an endogenous gene (or cDNA fragment) or a foreign gene (or cDNA fragment) isolated from any other source.

More specifically, the promoter constructs may be assembled according to the present invention by linking the wbeI fragment (preferably the BamHI-NcoI fragment (SEQ ID NO: 5, positions 2009–2798 of FIG. 2) or BamHI-PvuII (SEQ ID NO: 6, positions 2009–2807 of FIG. 2) in frame with desired genes (or DNA that codes for anti-sense RNA) transcriptionally fused to a polyadenylation sequence (e.g. nopaline synthase polyadenylation sequence). To be able to select for transformed cells/tissues, the constructed plasmid should desirably also encode a selectable marker (for example NPTII) under the control of a strong constitutive promoter. However, this may not be needed if the wbeI P2 promoter drives the expression of a selectable marker gene.

It should be kept in mind that the production of transgenic plants can only be achieved with explants that are totipotent, e.g. plant tissues containing cell types that are able to regenerate into a whole plant. Only a few sources of explants can be used in monocots for production of plants in vitro. So far, transgenic monocot plants have been derived from immature zygotic embryos forming embryogenic callus, microspore embryos and from inflorescence tissue. The culture conditions of the explant and the regeneration protocols vary between different plant species and have to be optimized for each genotype to be used for transformation.

It is particularly preferred that transgenic plants be produced from transformed scutellar tissue of zygotic embryos from which the embryo axis has been detached (e.g. as disclosed in U.S. Pat. No. 5,589,617 filed Aug. 3, 1994; the disclosure of which is incorporated herein by reference). This is because embryogenic cells of the zygotic embryo are located principally in the scutellum, and the removal of the embryo axis results in inhibition of the growth of non-embryogenic callus that competes for nutrients and other constituents of the tissue culture medium. Moreover, the need for tedious identification, selection and maintenance of the embryogenic callus from a mixture of different callus types is avoided. Thus, the promoter constructs of the present invention may be targeted into the competent cells of the scutellum and stably transformed somatic embryos and plants regenerated therefrom.

The scutellum may be isolated by any art-recognized technique; however, it is desirable to remove as much of the embryo axis as possible, while injuring the scutellum as little as possible This may be done, for example, using a stereomicroscope, scalpel blade (preferably Fishers size 11) and ordinary forceps. Alternatively, blades of different sizes or specially modified blades may be used for isolation of the scutella. In an immature embryo of appropriate stage selected for isolation, the scutellum appears as a transparent to creamy white shield-shape disk with its concave surface partially covering the embryo axis. The embryo axis with its pointed shoot and root apices is attached to the scutellum in the lower half. The most critical feature of the three step procedure described in this invention for isolation of scutellum is that it avoids any injury to the sensitive parts of the scutellum while removing the entire embryo axis.

While it is desirable that the embryo axis be entirely removed, and the scutellum uninjured, it will be appreciated that an imperfectly isolated scutellum may still offer somatic embryo regeneration potentially superior to that of intact embryos. The scutellum may be isolated at any stage that will yield enhanced regeneration relative to intact embryos.

The isolated scutella may be cultured in any medium suitable for the development of embryogenic cells and development of somatic embryos. However, the isolated scutella are preferably cultured in agar solidified MS (Murashige and Skoog, 1962) salt formulation containing 2–3 mg/l phytohormone 2,4-D and 100–200 mg/l vitamin-free casamino acid.

The zygotic embryo of most cereals is usually isolated from the kernels at about 8–14 days post anthesis. With wheat, the preferred time is 10–12 days and for barley 8–10 day old kernels are favored. This time period may differ between cultivars and it is therefore important to do systematic tests to determine the optimal age of the kernel for embryo isolation. The fragile nature of young embryos makes separation of the embryo axis from the scutellum difficult without causing extensive cell damage. Too much tissue injury may also reduce the quality of scutella isolated from older embryos, in which the embryo axis is more firmly attached to the scutellum.

Preferably, the embryos should not be isolated immediately after harvest of the kernels. A holding period of 5–15 days may be included, preferably at 5°–10° C. This refrigeration facilitates separation of the embryo from the kernel. It is not necessary to culture the embryos before isolation of the scutella.

To produce genetically engineered plants, the isolated scutellum may be transformed with the promoter constructs of the present invention. However, it is preferable to pre-culture the isolated scutella, typically for 2–5 days, prior to transformation. After two days, the cells of the scutellum are actively dividing, which is desirable. By 4–5 days, the scutella have developed hard embryogenic callus, making it more difficult to introduce the foreign DNA into embryogenic cells. Although genetic transformation can still occur at this stage, the resulting plants are likely to be chimeric.

For the purpose of the present invention, it is not critical which transformation technique is used, provided it achieves an acceptable level of gene transfer.

Listed below are references to different methods that have been successfully used to introduce exogenous DNA into monocot cells to produce transgenic plants. Transgenic rice and maize have been obtained using all three of the following methods for DNA delivery, whereas transformed oat, rye, wheat and barley have only been demonstrated by employing the particle bombardment technology.

Microprojectile bombardment: Vasil et al. 1992 (wheat), Vasil et al. 1993 (wheat), Weeks et al. 1993 (wheat), Becker et al. 1994 (wheat), Nehra et al. 1994 (wheat), Christou et al. 1991 (rice); Li et al. 1993 (rice), Gordon-Kamm et al. 1990 (maize), Fromm et al. 1990 (maize), Somers et al. 1992 (oat); Castillo et al. 1994 (rye), Wan and Lemaux 1994 (barley); Ritala et al. 1994 (barley) and Barcelo et al. 1994 (tritordeum).

Electroporation: Xu and Li 1994 (rice), Rhodes et al. 1988 and D'Halluin et al. 1992 (maize)

Direct DNA delivery into protoplasts: Shimamoto et al. 1989 (rice), Datta et al. 1990 (rice) and Hayakawa et al. 1992 (rice).

The literature articles referred to above are all incorporated herein by reference.

While the functionality of the P1 and the P2 promoters, respectively, to drive gene expression has been shown in wheat, barley, oat and maize cells so far, it is to be reasonably expected from the close relationship to other monocots of economic significance, e.g. rice, rye and sorghum, that the isolated promoters will function in these plant cells as well. This can be assumed from studies demonstrating that many monocot promoters express high levels of marker gene activity when tested in other monocot species. For example, the Act1 promoter isolated from rice has been used to produce transgenic wheat (Nehra et al. 1994). The maize ubiquitin 1 promoter was used for production of transgenic wheat (Vasil et al. 1993; Weeks et al. 1993), rice (Toki et al. 1992) and barley (Wan and Lemaux 1994). It is to be noted that the presence of intron sequences located between a promoter and a marker gene (as in the DNA sequence of the present invention) have in several cases been shown to enhance foreign gene expression in monocot cells (Callis et al. 1987; Vasil et al. 1989; McElroy et al. 1990). For example, expression of the chloramphenicol acetyltransferase (CAT) gene driven by the maize Adh1 promoter increased up to 100-fold when the Adh1 intron1 is positioned between the promoter and the marker gene (Callis et al. 1987). Stimulation of gene expression by introns in monocots does not require a promoter and intron from the same gene. Thus it has been found that the maize Adh1 intron 1 (Callis et al. 1987), the maize Sh1 intron 1 (Vasil et al. 1989; Maas et al. 1991), the maize Bz1 intron (Callis et al. 1987) stimulate transgene expression controlled from other promoters as well.

Both the P1 and the P2 promoters have been found to require intron sequences to efficiently drive expression of the GUS gene (see Examples 7 and 8 of the following disclosure). From reports showing that splicing of introns in monocots and dicots differ (Keith and Chua, 1986; Goodall and Filipowicz, 1991), it is not at present possible to make a clear prediction that the isolated promoter sequences of the present invention will function in dicot plant cells.

To provide examples of the usefulness of the present invention, listed below are some possible applications for the SalI-PvuII [SEQ ID NO:7] (position 1–2807 of [SEQ ID NO:1]) wbeI DNA fragment (or fragments thereof). The isolated wbeI sequences may be used, inter alia, to:

drive expression of anti-sense RNA;

drive expression of genes encoding a scorable product, e.g. the β-glucuronidase or luciferase genes;

drive expression of genes encoding a selectable marker, e.g. neomycin phosphotransferase (nptII) confering resistance to aminoglycosidic antibiotics such as Geneticin and paramomycin;

drive expression of genes encoding herbicide tolerance, e.g. glyphosate resistance or glufosinate resistance genes;

drive expression of genes affecting starch biosynthesis or modification e.g. starch branching enzyme, starch synthases, ADP-glucose pyrophosphorylase genes;

drive expression of genes involved in fatty acid biosynthesis, e.g. desaturase or hydroxylase genes.

drive genes encoding seed storage protein genes, e.g. glutenin genes;

drive expression of genes encoding insect resistance, e.g. crystal toxin protein gene of *Bacillus thuringiensis;* drive expression of genes encoding viral resistance, e.g. viral coat protein genes;

drive expression of genes encoding fungal resistance, e.g. chitinase, β-1,3-glucanase or phytoalexin genes;

drive genes altering malting and feed quality in barley, e.g. heat-stable β-glucanase or chymotrypsin inhibitor genes;

drive genes encoding valuable pharmaceuticals, e.g. antibiotics, secondary metabolites, pharmaceutical peptides or vaccines.

II. Specific Discussion of the development of the invention

The wbeI fragment on which the present invention is based was originally isolated from a genomic library of wheat (Triticum aestivum L. CV. Biggar) constructed in the vector λGEM11 (trademark—commercially available from Promega Corp. of 2800 Woods Hollow Road, Madison, Wis. USA, 53711-5399); see Båga, M., et al., "Molecular Cloning and Expression analysis of Peroxidase Genes from Wheat", Plant Mol. Biol. 29:647–662, 1995; the disclosure of which is incorporated herein by reference). A polymerase chain reaction (PCR) strategy was used to identify pools of the library containing type I starch branching enzyme genes (wbeI) One of the positive pools was further screened by plaque hybridization and resulted in the purification of the λBE64 clone shown in FIG. 1. The insert of λBE64 was found by restriction mapping, Southern blot hybridization and DNA sequencing to carry the 5' upstream region and the first half of a putative type I starch branching enzyme gene. Putative exons and introns were assigned from reverse transcriptase PCR (RT-PCR) experiments and sequence comparisons to cDNA clones encoding starch branching enzyme genes of rice and maize. All introns were bordered by consensus sequences for splice sites. The introns showed no, or very limited, DNA sequence similarity to corresponding introns in the rice gene referred to above. The 5' upstream regions of the wbeI gene and rice genomic clone were also different in their respective DNA sequences.

Part of the nucleotide sequence of the pBE64:8-2 clone (nucleotides 1–2959) [SEQ ID NO:1] is shown in FIG. 2 of the accompanying drawings. This clone was deposited on May 9, 1996 at the American Type Culture Collection, 12301 Parklawn Drive, Rockville, Md., 20852, USA, under the terms of the Budapest Treaty under deposit number ATCC 97544. The ATG codon (position 2037–2039), located 61 nucleotides downstream of a putative TATA box, is postulated to constitute the start of translation on P1 mRNA. The first 67 amino acids encoded by the P1 transcript are presumed to constitute a transit peptide, targeting the branching enzyme into chloroplasts and amyloplasts.

Figure 5:
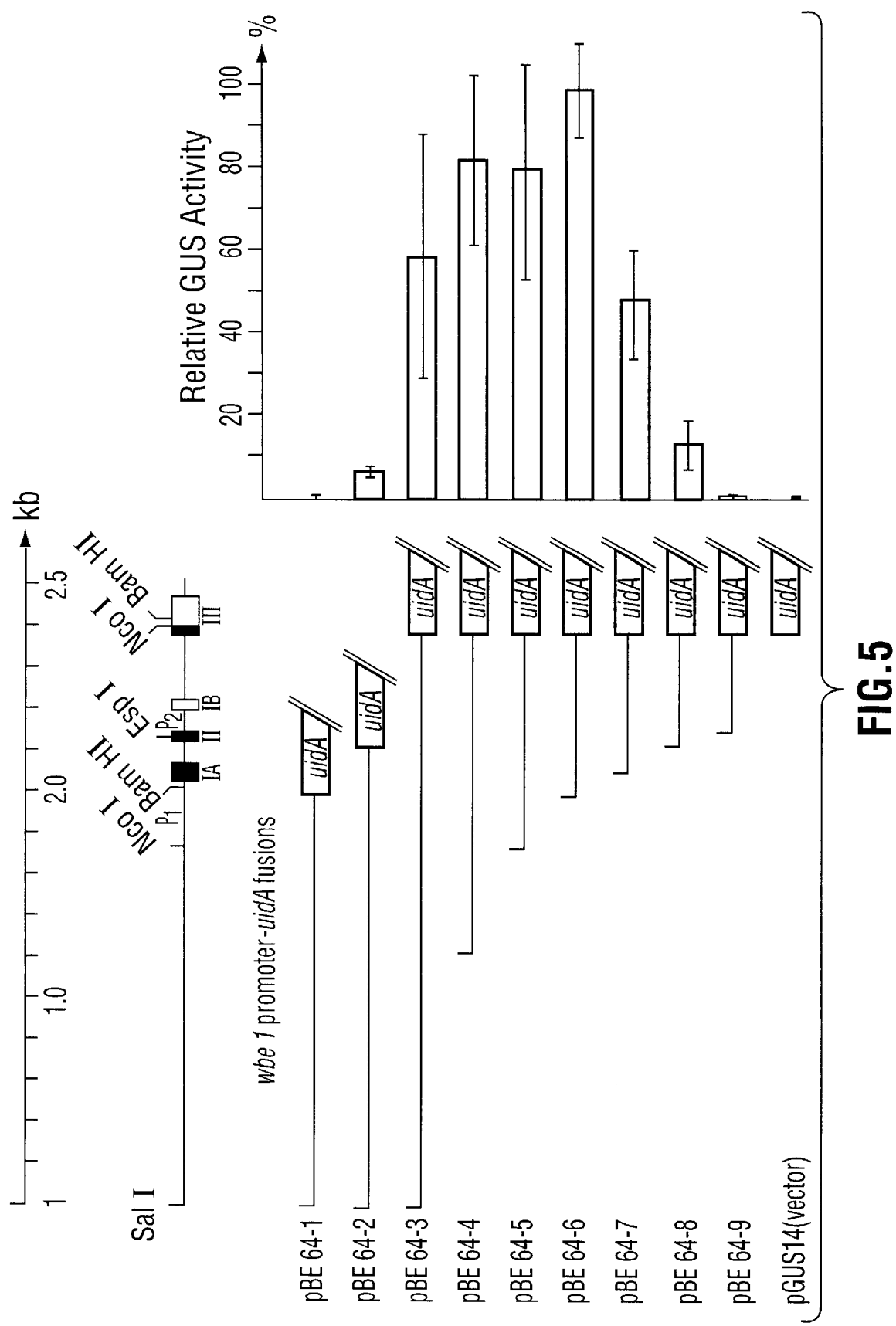
FIG. 5 is a comparison of relative transient GUS activities of wbeI-uidA fusion constructs in microprojectile bombarded wheat cells; the diagram at the top shows the wbeI upstream region and position of the P1 and P2 promoters; coding sequences IA, II, IB and III are indicated by boxes, in which filled areas refer to sequences coding for a putative transit peptide; below is shown wbeI promoter-uidA fusion constructs, where horizontal line indicates various wbeI fragments fused in frame with the uidA (GUS) coding sequence; histogram at the right shows a comparison of relative GUS activities of the different fusions expressed transiently in wheat cells; the values are presented as the percentage GUS activity expressed relative to construct pBE64-6 (100% =8.2 nmol MU produced $h^{-1}mg^{-1}$ protein) and data were obtained from at least three independent experiments.

In order to determine the promoter region of the fragment, various gene constructs were prepared containing different regions of the promoter fragment fused in frame with *Escherichia coli* uidA gene coupled to 3' termination signals from the nopaline synthase gene. The gene constructs thus prepared are represented in FIG. 5. The resulting plasmid DNA was introduced into cells in suspension culture, excised roots, leaves and scutella of wheat by particle bombardment. Expression of β-glucuronidase (GUS) activity was assayed 48 hours post-bombardment and compared by histochemical assay to that obtained with a constitutively expressed Act1D-GUS construct (McElroy, et al., "Isolation of Efficient Actin Promoter for Use in Rice Transformation," Plant Cell, 2:163–171, 1990; the disclosure of which is incorporated herein by reference).

Figure 4:
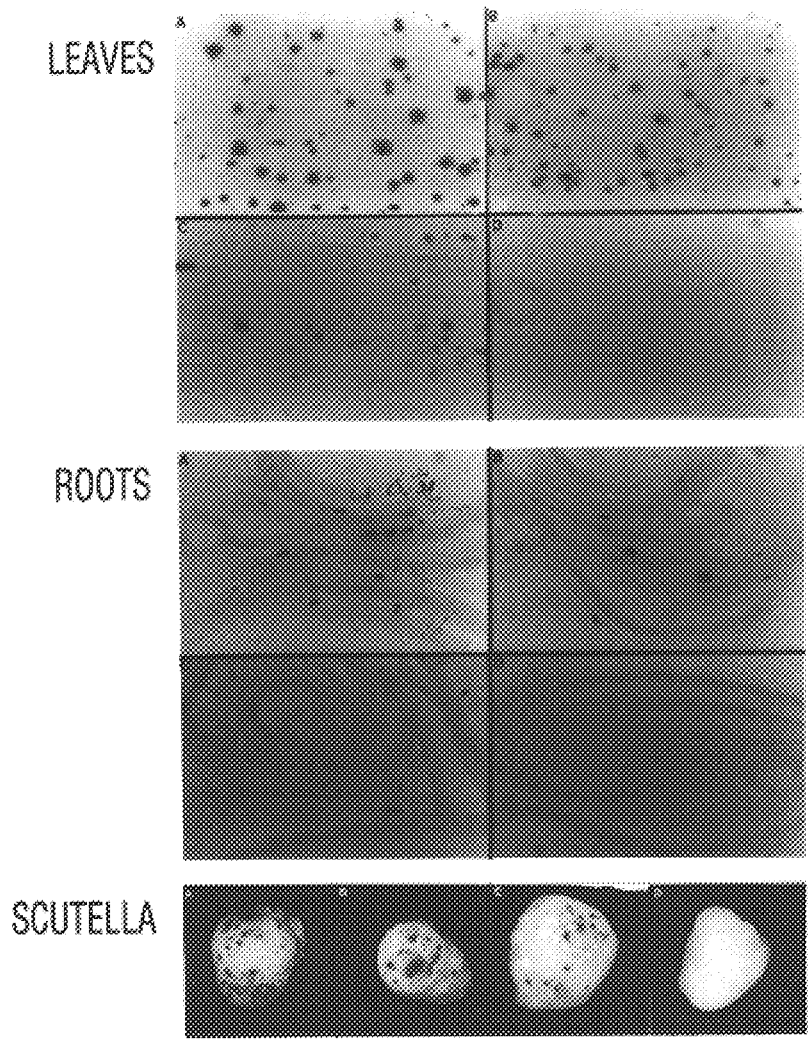
FIG. 4 shows the histochemical localization of transient GUS activity in wheat leaves, roots and scutellar tissues bombarded with constructs pAct1D-GUS (A), pBE64-6 (B), pBE64-3 (C), and pGUS14 (D), respectively.

The construct pBE64-3 contains the 1–2803 DNA sequence [SEQ ID NO:8] of the isolated promoter and was found to transiently express the marker gene in all tissues tested (FIGS. 4 and 5). Construct pBE64-6 containing the 1997–2803 fragment [SEQ ID NO:3] showed a higher level of transient expression than pBE64-3. The pBE64-6 GUS activity levels were approximately 20–50% of those obtained with the Act1D-GUS construct (data not shown) The promoter-less vector (pGUS14) did not show any significant levels of GUS activity.

To delineate the promoter fragments required for expression, a deletion analysis was performed. Different fragments of the wbeI promoter were used to form the other constructs shown in FIG. 3, i.e. pBE64–1, –2, –4, –5, –7, –8 and –9 and these constructs were tested by transient expression in wheat suspension cells. The results are shown in FIG. 5.

Construct pBE64-1 having the fusion point located 24 bp upstream of the assigned first ATG codon showed no significant level of GUS activity when compared with the promoter-less vector (pGUS14). The addition of sequences carrying intron 1a to pBE64-1 created construct pBE64-2 giving a seven-fold increase in expression level. The presence of both intron 1a and intron 2 (pBE64-3) gave an additional seven-fold increase of GUS activity. Thus the presence of intron sequences has a positive effect on expression of uidA gene driven by the wbeI promoter. However, further 5' deletion experiments showed that the entire 1–1991 region could be deleted (constructs pBE64-4, pBE64-5 and pBE64-6) without any negative effect on uidA expression. Therefore the majority of GUS activity observed in the construct pBE64-3 originates from a second promoter located downstream of position 1991. Further deletions from the 5' end of the wbeI gene delineated the second promoter to the 2251–2803 fragment (pBE64-8) [SEQ ID NO: 4].

In summary, therefore, the deletion analysis data show that the wbeI carries at least two promoters $P_1$ and $P_2$, of which $P_1$ directs weak expression of the GUS activity in wheat cells in suspension culture as shown by construct pBE64-2 (FIG. 5). The second promoter $P_2$, located within the intron 2, is strongly expressed in wheat cells (pBE64-6).

Gene expression vectors were constructed using the $P_1$ and $P_2$ promoter fragment fused to a scorable and selectable marker gene gus::nptII (FIG. 6) which codes for GUS and neomycin phosphotransferase (NPTII) activities, respectively. NPTII confers resistance to aminoglycosidic antibiotics such as GENITICIN (trademark). The gene expression vectors were biolistically delivered into cultured wheat cells and isolated scutella. Several GENITICIN-resistant transgenic wheat lines were produced. Southern hybridization revealed the integration of inserted genes into the wheat genome of the cell lines. The tested transgenic wheat cell lines show a high activity of the introduced gene (Table 2). Transgenic wheat plants have been obtained from regenerated bombarded scutella and are undergoing analysis for stable integration of the introduced fusion gene constructs.

In summary, therefore, it can be seen that the promoter fragment isolated from wheat can be used in the production of transgenic wheat. This promoter-intron-exon combination has been demonstrated to express various marker genes in cultured wheat cells as well as all parts of a wheat plant. A unique feature of the promoter fragment is that the transcription of genes under its control can start from two regions. This implies that there are at least two promoters, one located on the 5' region upstream of the exon 1A, and a second promoter located in intron 2. The promoter is useful for the expression of genes in wheat, barley, maize, oat, rice and other monocot plants.

Full details of the actual procedures and experiments carried out to develop and test the present invention are provided below.

MATERIALS AND METHODS

Chemicals

Restriction endonucleases were obtained from Boehringer Mannheim, Pharmacia or New England Biolabs. Alkaline phosphatase, T4 DNA ligase, Klenow fragment of DNA Polymerase I, Taq DNA Polymerase and herring sperm DNA were obtained from Boehringer Mannheim. T4 DNA Polymerase and deoxynucleoside 5'-triphosphates were obtained from Pharmacia. Radioactive nucleotides were obtained from DuPont-NEN. Oligonucleotides synthesized on a Model 394 DNA Synthesizer (Applied Biosystems) were supplied by the DNA Technologies Unit, National Research Council Canada, Saskatoon. Other chemicals were purchased from BDH, Biosynth AG, Difco Laboratories, Fisher Scientific or Sigma.

Cloning procedures

The procedures used for preparation of DNA, cloning and transformation were essentially as previously described (Sambrook et al. 1989; and Ausubel et al. 1994; the disclosure of which is incorporated herein by reference). The usage of restriction endonucleases, the Klenow fragment of DNA Polymerase I for fill-in of DNA fragments with 5' protruding ends, the T4 DNA Polymerase for blunt-ending DNA fragments with 3' protruding ends and alkaline phosphatase for removal of 5' terminal phosphate residues were carried out according to the supplier's intructions. Enzymes were inactivated by heating at 65° C. for 10 minutes when possible or by phenol/chloroform extractions followed by ethanol precipitation.

Separation of DNA fragments was performed by electrophoresis on agarose gels (0.76%–1.5%) containing 0.5 μg/ml ethidium bromide and 0.5×Tris-Borate-EDTA (TBE) running buffer (1×TBE is 0.89M Tris-borate, 0.002M EDTA). The separated DNA fragments were visualized and photographed using a FOTODYNE® UV trans-illuminator equipped with a Polaroid® MP-4 Land Camera. DNA fragments were isolated from agarose gels using DEAE-cellulose membranes according to the manufacturer's (Schleicher and Schuell) instructions.

Ligations involving plasmid DNA were done for three hours at room temperature using a PEG ligation buffer as described (King and Blakesley, 1986). PCR products were cloned into a T-vector prepared as described by Marchuk et al. (1991).

Competent *Escherichia coli* DH5α (Hanahan 1983) cells were prepared according to Inoue et al. (1990) and stored at −70° C. until used. Transformations were according to standard protocols and transformants were selected on solid Luria broth (LB) medium containing 75 μg/ml ampicillin.

DNA isolation

Mini-scale preparations of plasmids were done from 1.5 ml cultures using the alkaline lysis procedure (Sambrook et.al, 1989). Larger scale preparations of plasmids to be used for cloning, DNA sequence analysis and particle bombardments were from 5, 150 or 500 ml cultures. The bacterial cells were lysed by alkaline lysis and purified on QIAGEN®-tips (tip 20, tip 100 or tip 500 depending on the volume of the culture) following the procedure recommended by the supplier (Qiagen).

Lambda DNA was isolated from lambda lysates prepared from cells grown on agarose plates according to Sambrook et al. (1989). Phage from 100 ml lysate were lysed and DNA was prepared using a QIAGEN-tip 500 (Qiagen) following the protocol supplied with column.

Total wheat DNA was isolated from leaves (15 g) of two week old plants using the method of Doyle and Doyle (1990).

Growth of plant suspension cultures and wheat plants

The wheat and barley suspension cell lines were established from callus derived from immature embryos of the wheat (*Triticum aestivum* L.) breeding line HY320 and the barley (*Hordeum vulgare* L.) cultivar Heartland, respectively. The maize cell line (Black Mexican Sweet) and the oat line (S229-5) were provided by D. A. Somers (University of Minnesota, Minn., USA). Wheat and barley cells were grown in MS medium (Murashige and Skoog, 1962) supplemented with B5 vitamins (Gamborg et al., 1968) and $5\times10^{-6}$M 2,4-dichlorophenoxyacetic acid (2,4-D). The growth medium for the maize and oat cell lines consisted of MS medium supplemented with E5 vitamins, 150 mg/l L-asparagine and $9\times10^{-6}$M 2,4-D. The cell lines were grown in 250 ml flasks on a gyratory shaker (150 rpm/min) under a light intensity of 5.5 μmol m$^{-2}$sec$^{-1}$ and maintained by weekly transfers of 15 ml culture to 50 ml fresh medium.

Wheat plants were grown in pots (15 cm diameter) in a growth room maintained at 25° C. day and 20° C. night temperatures and 65% relative humidity. Light was provided by white fluorescent tubes and incandescent bulbs with a light intensity of 150 μmol m$^{-2}$ sec$^{-1}$ under a 16 hour photoperiod. Plants were fertilized weekly with a N:P:K (20:20:20) solution (0.25 g/l).

Plants were grown under aseptic conditions by germinating surface-sterilized seeds in 75 ml glass tubes containing 15 ml MS medium supplemented with B5 vitamins. The seeds were surface-sterilized by vigorous shaking in 5.25% NaOCl solution for 30 min and rinsed extensively with sterile water.

DNA hybridization techniques

DNA fragments to be analyzed by Southern blot hybridization were separated on 1.0% agarose gels, depurinated, denatured and neutralized as described by Sambrook et al. (1989). The nucleic acids were transferred onto Hybond-N membranes (Amersham) using a PosiBlot Pressure Blotter® (Stratagene). After a brief rinse of the membrane in 2×SSPE (1×SSPE is 0.18M NaCl, 10 mM $Na_2PO_4$ pH 7.7, 1 mM EDTA), the nucleic acids were cross-linked to the filter using a Stratalinker (Stratagene). Filters were prehybridized for 3 hours in 25 ml hybridization solution [5×SSPE, 50% deionized formamide, 1% SDS, 5×Denhardt's solution (1×Denhardt's solution is 0.02% Ficoll, 0.02% polyvinylpyrrolidone, 0.02% bovine serum albumin), 100 µg/ml fragmented and heat-denatured herring sperm DNA] using a Hybaid Hybridization Ovens® (Hybaid) set at 42° C. The hybridization was for 15 h at 42° C. in 25 ml hybridization solution containing 1–5×$10^6$ dpm/ml heat-denatured probe. Radiolabelling of the BE12/BE13 probe (FIG. 1) was done by incorporation of [$\alpha$-$^{32}$P]dCTP using the Prime-a-Gene® System from Promega. The membrane was washed twice at room temperature with 2×SSPE, 1% SDS for 5 min followed by two 10 min washes at 42° C. with 1×SSPE, 0.1% SDS. Exposure of membrane to X-ray film was at –70° C. for 1 hour to 1 week depending on the intensity of hybridizing signals.

Plaque hybridization was initiated by immobilizing phages from 9 cm culture dishes (4000 plaques/plate) onto BA85 nitrocellulose membranes (Schleicher and Schuell) as described by Sambrook et al. (1989). The filters were hybridized under conditions described for Southern blot hybridization, using 0.5–1×$10^5$ dpm/ml of radiolabelled BE12/BE13 (FIG. 1) probe. Filters were washed twice at room temperature for 5 min with 2×SSPE, 0.1% SDS and for 10 min at 50° C. with 1×SSPE, 0.1% SDS. An additional 10 min wash at 55° C. with 1×SSPE, 0.1% SDS was performed when background signals were high. Filters were exposed to X-ray films for 4–12 hours at –70° C. Agarplugs containing positive plaques were picked and replated to about 400 plaques/dish. The hybridization step was repeated for two additional rounds to yield well isolated positive plaques. A single plaque was used for making a phage stock solution as described by Sambrook et al. (1989).

Isolation of RNA and synthesis of first-strand cDNA

Plant material used for RNA extraction was collected from leaves (5 g) and roots (5 g) of two week old plants, seeds (1 g) at 12 days after anthesis and wheat suspension cells (5 g). The samples were frozen in liquid nitrogen and stored at –70° C. until extraction of RNA was performed using a modified hot-phenol method. The samples were ground to a fine powder in liquid nitrogen using pestle and mortar and extracted for 10 min at 65° C. with 10 ml pre-heated extraction buffer (50 mM NaAc pH 4.5, 20 mM EDTA, 2% SDS, 50 mM 2-mercaptoethanol) : acidic phenol (1:1). After cooling on ice for 5 min, the extract was centrifuged at 15000×g for 10 min at 4° C. The upper aqueous phase was re-extracted twice with hot phenol followed by a final extraction with chloroform/isoamyl alcohol (24:1). Extracted RNA was precipitated at –20° C. after addition of 0.1 vol 3.0M NaAc pH 4.5 and 2.5 vol EtOH. The RNA was pelleted by centrifugation at 15000×g for 15 min at 4° C., washed at room temperature with 3.0M NaAc pH 5.2 as described (Logemann et al. 1987) and finally washed with 80% EtOH. The RNA pellet was resuspended in 50 mM NaAc pH 7.0, 1 mM EDTA and total RNA concentration was determined by spectrophotometry.

Poly(A)$^+$ RNA was isolated from 500 µg total RNA using a Oligotex-dT mRNA kit (Qiagen) and used for first-strand cDNA synthesis. One µg poly(A)$^+$ RNA was primed with 0.5 µg oligo(dT)$^{12-18}$ (Pharmacia) and reverse transcribed using 200 units Superscript II (Gibco-BRL) following the protocol supplied by Gibco-BRL. Synthesized cDNA was purified by extraction with phenol/chloroform/isoamyl alcohol (25:24:1) followed by an extraction with chloroform/isoamyl alcohol (24:1) and passage over a Sephacryl S300 spun column (Pharmacia) equilibrated with 20 mM NaAc pH 7.0, 60 mM NaCl. The yield of first-strand cDNA was calculated from the fraction of radiolabelled [$\alpha$-$^{32}$P]-dCTP incorporated into the synthesized cDNA.

The invention and the way in which it was derived by the inventors are described in more detail below by means of the following Examples, which should not be taken as limiting the scope of the invention.

EXAMPLE 1

Construction of a wheat genomic library

Total wheat DNA (1 mg) was partially digested with Sau3A (0.015 units/µg DNA) and generated fragments were loaded onto two 38 ml 10–40% linear sucrose gradients made up in 20 mM Tris-HCl pH 7.5, 10 mM EDTA buffer. The gradients were centrifuged in a SW-28 rotor at 15° C., 25000 rpm for 24 h followed by collection of 1 ml fractions. Fractions enriched for 15–23 kb DNA fragments were pooled, diluted three-fold and ethanol precipitated twice to remove excess sucrose. The DNA fragments were loaded onto a 13 ml sucrose gradient (10–40%) and centrifuged at 15° C. in a SW-40 rotor for 17 h at 28000 rpm to further enrich fragments of desired size. A fraction of the size-fractionated DNA (0.76 µg) was ligated to 1 µg dephosphorylated BamHI arms of the phage vector λGEM-11 (trademark; Promega) for 14 h at +4° C. in a 8 µl reaction containing 6 mM Tris-HCl pH 7.5, 6 mM NaCl, 6 mM $MgCl_2$, 0.05% gelatine, 1 mM DTT, 1 mM ATP and 1 Weiss unit of T4 DNA ligase. The ligated DNA was packaged using GIGAPACK II PLUS® extracts following the protocol provided by the supplier (Stratagene). To facilitate the subsequent screening of the library, the packaged material was used for 68 individual transfections of the host strain *Escherichia coli* XL1-BlueMR (Stratagene). The generated library consisted of 68 pools that contained 3×$10^6$ primary clones with a vector background of 0.03%. The average insert size was 17 kb.

EXAMPLE 2

Screening of genomic library

Pools of the constructed genomic library were screened for type I starch branching enzyme sequences using a PCR strategy followed by screening of one positive pool by plaque hybridization. The primers BE12 (5'GAGACTACACCATGGCAACAG-3') [SEQ ID NO: 9] and BE13 (5'-TCCATGATTGCCATCAGC-3') [SEQ ID NO:10] used in the PCR analysis were designed based on amino acid sequences of type I starch branching enzymes from rice (Nakamura and Yamanouchi, 1992; Kawasaki et al. 1993) and maize (Baba et al. 1991), and correspond to sequences located on the third and sixth coding regions (FIG. 1). PCR analysis with the BE12/BE13 primer pair and total wheat genomic DNA as template gave two specific products of 1.15 and 1.25 kb (FIG. 3; lane W), respectively, of which the 1.25 kb fragment was used as probe in subsequent hybridizations. Phage lysate was extracted from five μl ($10^{10-10^{11}}$ phage) of each library pool (Kawasaki, 1990) and used as template in the subsequent PCR amplification. The PCR mixtures contained 5.0 μl of the prepared lysate (or 0.5 μg total wheat DNA), 1×PCR buffer (10 mM Tris-HCl pH 8.3, 50 mM KCl, 1.5 mM $MgCl_2$, 0.01% gelatine), 0.2 mM dNTP, 0.5 μM of each primer and 0.6 units of Taq DNA Polymerase in a total volume of 25 μl overlaid with 25 μl mineral oil. A DNA Thermal Cycler® (Perkin-Elmer) was used for the PCR amplifications, which were initiated by a denaturation step at 94° C. for 5 min followed by 30 cycles of 1 min at 94° C., 1 min at 55° C. and 2 min at 72° C. After a final extension step at 72° C. for 7 min, the generated products were analyzed by Southern blot hybridization using radiolabelled BE12/BE13 fragment (FIG. 1) as probe. The screening of the pools showed that 13 pools of the library contained putative type I starch branching enzyme genes. Eight of the pools gave a positive signal of 1.25 kb, whereas the remaining four pools hybridized to a 1.15 kb PCR product (data not shown). One of the pools that gave a 1.25 kb product was screened by three rounds of plaque hybridization to give the purified clone λBE64 (FIG. 1).

EXAMPLE 3
Construction of pBE64:8-2 and characterization of the insert by DNA sequence analysis The isolated genomic clone λBE64 was digested with SalI, XhoI, SacI, EcoRI, HindIII and BamHI in both single and double enzyme combinations to obtain a preliminary restriction map of the insert. FIG. 1 shows positions of mapped SalI fragments, of which a 5.0 kb fragment was found by Southern blot hybridization to hybridize to the BE12/BE13 (FIG. 1) probe. The 5.0 kb SalI fragment was isolated and cloned into the SalI site of pUC19 (commercially available from various well-known suppliers, e.g. Boehringer Mannheim, Pharmacia, United States Biochemical, Biolabs, Clontech and Gibco BRL) to give construct pBE64:8-2 (FIG. 1), which was extensively mapped using a variety of different restriction endonucleases. Suitable restriction sites were used for construction of cutback derivatives of pBE64:8-2 and for cloning of fragments to be DNA sequenced. The DNA sequence analyses were performed using a TAQ/DYE-DEOXY TERMINATOR CYCLE® kit (Applied Biosystems) and products were analysed on a Model 373 Automated DNA Sequencer (Applied Biosystems) according to the supplier's instructions. The nucleotide sequences of both strands of overlapping clones were assembled and analysed using the EUGENE® (Baylor College of Medicine, Houston) computer software. Comparison of the generated DNA sequence to nucleotide sequences of type I starch branching enzyme clones isolated from rice and maize allowed assignment of putative coding regions IA, II, III, IV, V and VI (FIG. 1). Coding region 1B was identified from reverse transcriptase PCR (RT-PCR) analysis of RNA expressed from cells carrying construct pGK105 or pGK107 (see Example 9). The DNA sequence of the 1–2959 region [SEQ ID NO:1] of the 5.0 kb SalI fragment is presented in FIG. 2.

EXAMPLE 4
Expression analysis of type I starch branching enzyme

Figure 3:
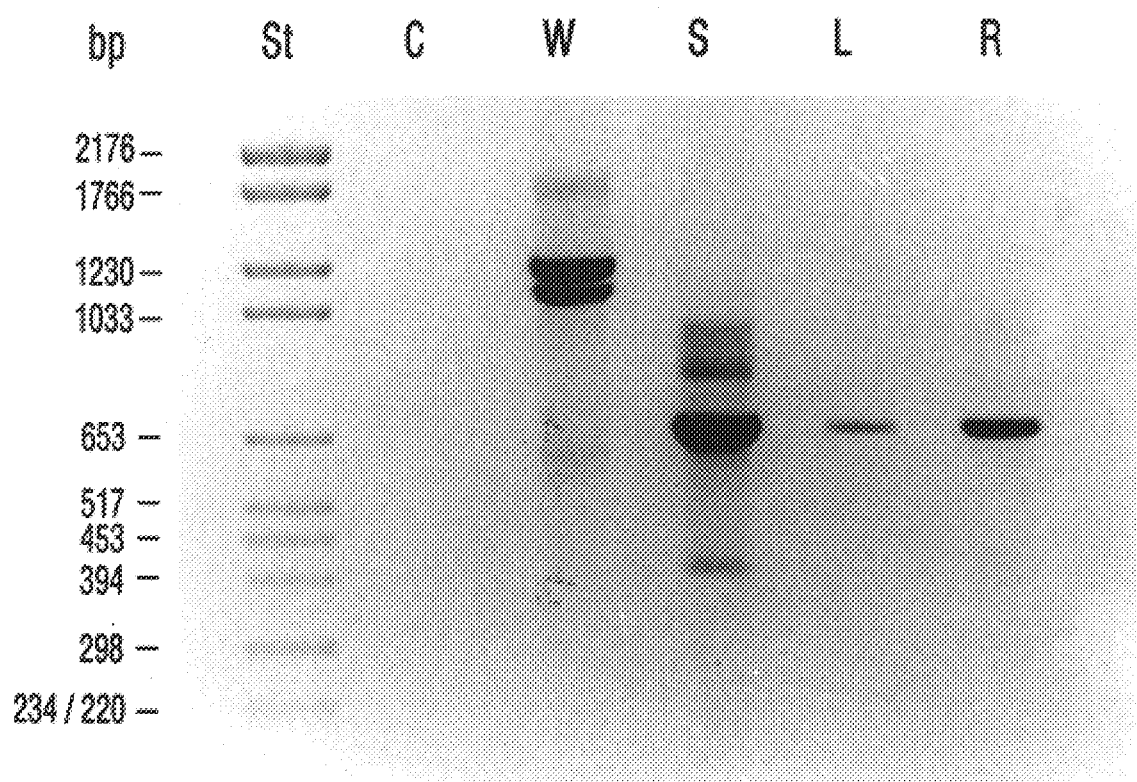
FIG. 3 shows the results of an RNA analysis of type I starch branching enzyme expression in wheat tissues; RT-PCR products obtained from reaction with BE12/BE13 primers [SEQ ID NOS: 9 and 10, respectively] and seed (S), leaf (L) and root (R) RNA as template are shown; DNA fragments produced in PCR reactions with wheat genomic DNA (W) as a template and reaction without a template (C) are also shown; the migration of molecular size marker (St) is indicated to the left.

To study if the isolated gene (wbeI) was expressed in wheat, RNA from various tissues was analyzed by RT-PCR. Poly(A)$^+$ RNA isolated from roots, leaves and seeds was reverse transcribed and analysed by PCR using primers BE12 and BE13 (FIG. 1). PCR amplifications were performed with a DNA Thermal Cycler (Perkin-Elmer) in 50 μl reaction mixtures that contained about 3 ng first-strand cDNA, 10 mM Tris-HCl pH 8.3, 50 mM KCl, 1.5 mM $MgCl_2$, 0.01% gelatine, 0.01% NP-40, 0.01% TWEEN® 20, 0.2 mM dNTP and 1.0 μM oligonucleotides. Two units of Taq DNA Polymerase was added to the reactions after an initial denaturation step at 94° C. for 5 min. The amplification reaction was for 30 cycles of 45 sec at 94° C., 45 sec at 63° C. and 2 min at 72° C. followed by a final extension at 72° C. for 7 min. Analysis of the amplification products by gel electrophoresis showed that cDNA of seed, leaf and root produced a 0.7 kb DNA fragment (FIG. 3, lanes S, L and R). The major RT-PCR products obtained from the different samples were isolated, cloned into a T-vector and analysed by DNA sequencing. Results indicated that different isoforms of type I starch branching enzymes were expressed in the various tissues. One DNA sequence variant of the RT-PCR products was common to all tissues tested and corresponded exactly over its entire 688 bp DNA sequence to the translated sequence predicted for wbeI. This information confirmed the assigned splice junctions located between the priming sites for BE12 and BE13 and strongly suggested that wbeI is active in several tissues of wheat.

EXAMPLE 5
Transient expression analysis of wbeI expression in wheat tissues

The wheat tissues (roots, leaves and scutella) used for transient expression assays were isolated from two week old plants grown under aseptic conditions and from seeds collected 12 days post anthesis. Roots and leaves were cut into 2 cm segments and placed on filter papers moisted with liquid MS medium just prior to bombardment. The seeds were surface-sterilized through treatments with 70% EtOH for 1 min and 1.0% NaOCl for 20 min followed by several rinses with sterile distilled water. Immature embryos were aseptically removed from the seeds and the scutella tissues were isolated by excision of the embryo axis from the embryos. The isolated scutella were precultured for two days on solid MS$^{++}$ medium (MS medium supplemented with B5 vitamins, 110 mg/l casamino acids and $1 \times 10^5$M 2,4-D; Nehra et al. 1994) prior to bombardment.

Gold particles (1 μm; Bio-Rad Laboratories) were washed and coated with the constructs pAct-1D (McElroy et al. 1990), pBE64-6 (FIG. 3), pBE64-3 (FIG. 3) and pGUS14 (FIG. 3), respectively, using $CaCl_2$ and spermidine as described by Sanford et al. (1993). For each bombardment, 0.5 mg particles coated with 0.8 μg plasmid were loaded onto a micro-carrier and introduced into the cells using a BIOLISTIC PDS-1000® helium device (Bio-Rad Laboratories) equipped with a 1100 psi rupture disc. Following bombardment, leaves and roots were incubated in liquid MS medium supplemented with B5 vitamins and scutella were incubated on solid MS$^{++}$ medium. After 48 h incubation in the dark at 25° C., the tissues were analysed for GUS activity by histochemical staining using X-Gluc as substrate (Jefferson et al. 1987). To facilitate visualization of GUS spots in leaves, the stained tissues were incubated in 80% EtOH to remove chlorophyll.

The transient expression analysis showed that the wbeI promoter fragment carried by pBE64-6 is able to drive expression of uidA in leaves, roots and scutella tissues (FIG. 4). The expression levels of pBE64-6 in the various tissues were about 20–50% of those expressed by the pAct-1D construct (data not shown). The pBE64-3 construct expressed lower levels of GUS activity than the pBE64-6 fusion in all tissues tested. No GUS activity (blue spots) was seen in tissues bombarded with the promoter-less vector, pGUS14.

EXAMPLE 6
Construction of chimeric genes

A. Construction of chimeric genes used in the transient expression assays.

The vector pGUS14 was assembled in two steps. First, the 1.9 kb SalI-EcoRI fragment carrying the β-glucuronidase gene (uidA) was isolated from pRAJ275 (Clontech) and inserted into the corresponding sites of the pUC18 vector (commercially available from various well-known suppliers, e.g. Boehringer Mannheim, Pharmacia, United States Biochemical, Clontech and Gibco BRL) to give construct pGUS10. Plasmid pGUS10 was digested with EcoRI, filled-in and ligated with a 0.33 kb Ecl136III—Ecl136III fragment carrying the nopaline synthase polyadenylation sequence from plasmid pBI221 (Clontech) and part of the multiple cloning site from pBluescript SK(+) (Stratagene). The resulting construct gave pGUS14 with unique HindIII, SphI, SalI, HindII, AccI and NcoI sites located upstream of uidA and unique SmaI, BamHI, SpeI, XbaI, NotI and SacII sites positioned downstream of the polyadenylation sequence.

Vector pGUS14 was used for insertion of DNA fragments isolated from pBE64:8-2 (FIG. 1) to give various wbeI promoter-uidA fusions (FIG. 5). These constructs were obtained as follows.

The pBE64:8-2 plasmid was restricted with BamHI followed by fill-in of generated ends. The digest was further restricted with SalI and the SalI-BamHI fragment (sequence 1–2013) SEQ ID NO: 11] was isolated and inserted into filled-in AccI site of pGUS14 to give construct pBE64-1. The pBE64-2 fusion was obtained by isolation of the SalI-EspI fragment (sequence 1-2253) [SEQ ID NO: 12], fill-in of ends and insertion into filled-in AccI site of pGUS14. Construct pBE64-3 was created by insertion of the NcoI-NcoI fragment (sequence 1759–2803) [SEQ ID NO: 13] into the NcoI site of pBE64-2. The pBE64-5 plasmid was obtained by insertion of the same NcoI-NcoI fragment into the NcoI site of pGUS14. Restriction of pBE64-5 with AccI, partial fill-in and dephosphorylation of ends followed by ligation with AccI-AccI (sequence 1235–2320) [SEQ ID NO:14] fragment generated construct pBE64-4. Fusion pBE64-6 was obtained by restricting pBE64-3 with HindIII and ApaI, blunt-ending the ends and religation. To create plasmid pBE64-7, the pBE64:8-2 plasmid was first cleaved with AvaII followed by fill-in of ends, restriction with NcoI, isolation of the AvaII-NcoI fragment (sequence 2122–2803) [SEQ ID NO:15], which was inserted between filled-in HindIII site and the NcoI site on pGUS14. Restriction of pBE64-3 with SalI and EspI followed by fill-in of ends and religation generated construct pBE64-8. Construct pBE64-9 was obtained by restricting pBE64-5 with AccI, fill-in of ends and religation. As shown in Table 1 below, all the fusion points between wbeI sequences and uidA were confirmed by DNA sequencing and showed that the wbeI coding sequences were fused in frame with uidA.

TABLE 1

DNA sequence at wbeI—uidA fusion points

| Construct | |
|---|---|
| | BamHI/AccI |
| pBE64-1 | ACAATGGGATCCGACC.ATG.GTC.CGT.<br>[SEQ ID NO: 16]<br>EspI/AccI |

TABLE 1-continued

DNA sequence at wbeI—uidA fusion points

| Construct | |
|---|---|
| pBE64-2 | .GTG.CGG.CTG.ACG.ACC.ATG.GTC.CGT.<br>[SEQ ID NO: 17]<br>NcoI/NcoI |
| pBE64-3 to pBE64-9 | .TAC.ACC.ATG.GTC.CGT.CCT.GTA.<br>[SEQ ID NO: 18] |

Note:
The DNA sequence of wbeI is shown in bold; the start codon for uidA is underlined.

B. Construction of chimeric genes used for stable transformation.

Figure 6:
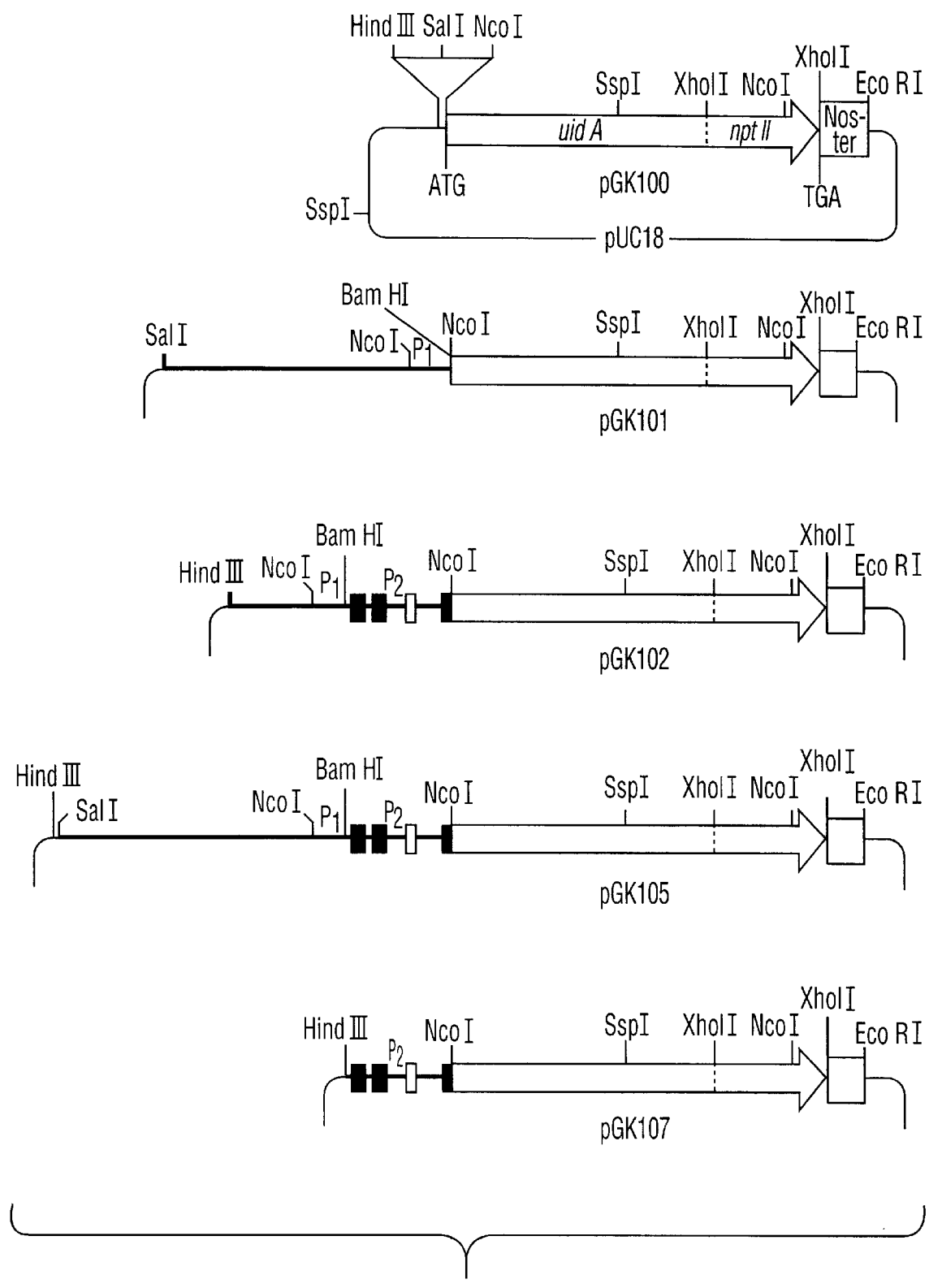
FIG. 6 is a schematic representation of wbeI-uidA::nptII fusion constructs; at the top is shown the vector pGK100 carrying the marker/selection gene (uidA::nptII) linked to the nopaline synthase polyadenylation sequence; below is shown fusions of various wbeI promoter sequences (thick line) linked in frame with uidA::nptII.; the location of the promoters P1 and P2 and coding regions (boxes) are indicated.

To obtain wbeI-uidA::nptII fusions (FIG. 6), a vector construct with suitable cloning sites located in front of the marker/selection gene was created first. This vector was obtained by isolating the 2.0 kb SspI-SspI and the 1.9 kb SspI-EcoRI fragments from pGUS14 and ligating these with isolated 1.2 kb SspI-EcoRI fragment from pGKK14 (Datla et al., 1991). The resulting plasmid was named pGK100 (FIG. 6). Construct pGK101 was obtained by ligating SspI digested pBE64-6 with SspI restricted pGK100 and followed by digestion with SpeI to digest religated pGUS14 before the transformation step. The fusion pGK102 was obtained in a similar way as pGK101, using SspI digested pBE64-6 in the ligation step. Insertion of the 2.0 kb SalI-BamHI fragment of pGK101 into corresponding sites of pGK102 yielded fusion pGK105. Construct pGK107 was created by digesting pGK105 with BamHI and SalI, fill-in of ends and religation of vector fragment.

EXAMPLE 7
Transient expression analysis of wbeI-uidA fusions

Three day old wheat suspension cells used for the transient expression studies were filtered through a 500 μm sterile sieve to remove larger cell clumps. Filtered cells (about 100 mg wet weight) were spread on a filterpaper (4 cm diameter) and placed onto solid MS medium supplemented with B5 vitamins and $5\times10^{-6}$M 2,4-D. The tungsten particles (1 μm, 3.0 mg) used as carriers of DNA were coated with 3 pmol plasmid using a calcium-spermidine precipitation method described by Sanford et al. (1993). About 0.75 mg of coated particles were used per bombardment, which was carried out as described in Example 5. Bombarded cells were incubated in the dark at 25° C. for 48 hours followed by preparation of cell extracts and determination of GUS activity by a fluorometric assay using 4-methylumbelliferyl-β-O-glucuronide as substrate (Jefferson et al. 1987). The protein concentrations of the prepared extracts was determined by the dye-binding method of Bradford (1976) using a kit from Bio-Rad Laboratories. Fluorescence was quantified on a Perkin Elmer Luminescence Spectrometer LS 50 with excitation at 365 nm, emission at 455 nm and a slit width of 5.0 nm. GUS activity expressed from the different fusions was determined from at least three independent assays, in which each sample was analysed in duplicate.

Analysis of GUS expression from the various deletion constructs demonstrated that the assigned P1 promoter was accompanied by another promoter (P2) located downstream of the EspI site (FIG. 5). This conclusion was drawn from analysis of constructs pBE64-2 and pBE64-8, both expressed significant GUS activities although the two fusions did not carry any wbeI sequences in common. A more precise location of the two identified promoters (FIGS.

1 and 2) was first postulated from analysis of the DNA sequence and subsequently confirmed by RT-PCR analysis (Example 9). The P1 promoter was found to be dependent on the 2014–2253 region carrying coding region I, intron 1a and part of coding region II for activity, as deletion of this DNA segment from pBE64-2 to give fusion pBE64-1 resulted in loss of GUS activity.

The highest level of P2 activity was obtained from construct pBE64-6. Deletions from the 5' end of wbeI sequences carried by pBE64-6 to give fusions pBE64-7, pBE64-8 and pBE64-9 resulted in a gradual decrease in P2 promoter activity to almost background levels for construct pBE64-9. These data demonstrated that the P2 promoter is dependent on the 2014–2253 region [SEQ ID NO:19] for efficient expression. The presence of the P1 promoter and its 5' upstream region appeared to have some negative effect on transient P2 expression as GUS activity from pBE64-3 was lower than measured for pBE64-6. The P2 promoter was also found to be dependent on sequences located downstream of the P2 promoter for efficient expression. A 3' deletion derivative of pBE64-6 with the IB coding region fused in frame with the uidA gene showed hardly any GUS activity when compared to pBE64-6 (data not shown), indicating that presence of intron 1b with flanking exon sequences stimulated expression driven by the P2 promoter.

EXAMPLE 8

Generation of stably transformed wheat cell lines and analysis of GUS activity

Coating of particles with the constructs pGK105, pGK107 and pGK100 (FIG. 6), respectively, was as described for transient expression, with the exception that gold particles were used instead of tungsten particles. Cells were prepared and bombarded as described in Example 7. Bombarded cells carried on a filter paper were incubated for two days in the dark at 25° C. on MS medium supplemented with B5 vitamins and 5×10⁶M 2,4-D. The filters carrying the cells were thereafter transferred every week to 6 cm culture dishes containing 0.6 ml liquid MS medium supplemented with B5 vitamins, 2,4-D and increasingly higher concentration of GENETICIN® (Gibco-BRL). The first selection step was at 10 mg/l GENETICIN followed by concentrations of 20, 25, 30 and finally 40 mg/l. During the time of selection on 30 mg/l and 40 mg/l GENETICIN, rapidly growing cell clumps emerged among cells bombarded with the pGK105 and pGK107 constructs. No foci of fast growing cells developed among cells bombarded with pGK100 or uncoated particles. The putatively transformed cell clumps were isolated and placed on solid selection medium containing 40 mg/l GENETICIN and maintained by monthly transfers to fresh selection medium.

Southern blot analysis of six of the generated cell lines confirmed that introduced DNA had integrated into the plant DNA (data not shown). Assay of GUS activity expressed by the different cell lines was determined by the fluorometric assay as described in Example 7. Values of GUS specific activity expressed by 11 cell lines transformed with pGK105, 12 cell lines carrying pGK107 and untransformed cells are presented in Table 2.

TABLE 2

Analysis of GUS activity in transgenic wheat cell lines

| GK105 Transformants | | GK107 Tranformants | | Untransformed | |
|---|---|---|---|---|---|
| Cell Line | GUS Activity | Cell Line | GUS Activity | Cell Line | GUS Activity |
| GK105-1:2 | 10.8 | GK107-12:1 | 13.2 | HY320 | 0.00–0.08* |
| GK105-1:3 | 4.9 | GK107-12:3 | 5.2 | | |
| GK105-1:4 | 3.1 | GK107-12:4 | 7.5 | | |
| GK105-1:8 | 4.8 | GK107-12:7 | 27.6 | | |
| GK105-1:9 | 9.9 | GK107-12:11 | 24.4 | | |
| GK105-1:10 | 3.4 | GK107-12:12 | 59.4 | | |
| GK105-1:11 | 8.8 | GK107-12:14 | 54.6 | | |
| GK105-1:12 | 3.7 | GK107-12:15 | 27.8 | | |
| GK105-1:13 | 4.8 | GK107-13:1 | 31.4 | | |
| GK105-1:14 | 7.2 | GK107-13:5 | 12.2 | | |
| GK105-1:15 | 7.8 | GK107-16:1 | 19.1 | | |
| | | GK107-16:2 | 19.2 | | |
| Average: | 6.3 | Average: | 25.1 | Average: | 0.05 |

GUS specific activity was determined in stably transformed wheat cell lines carrying the fusion construct GK105 or GK107. The assay was performed using a fluorometric method as described (Jefferson et al. 1987). Activity values are presented as nmol MU produced min⁻¹ mg⁻¹ protein.
*Values given represent range of activity obtained from five independent assays performed with the untransformed cell line.

Cell lines transformed with the pGK107 constructs expressed on an average a four-fold higher level of GUS activity than cell lines harboring pGK105. Untransformed cells showed negligible levels of GUS activity. These data suggested that expression from the wbeI promoters is stronger when the P2 promoter is alone than when both the P1 and P2 drive expression.

EXAMPLE 9

RT-PCR analysis of wheat cell line stably transformed with pGK105 and pGK107.

Figure 7:
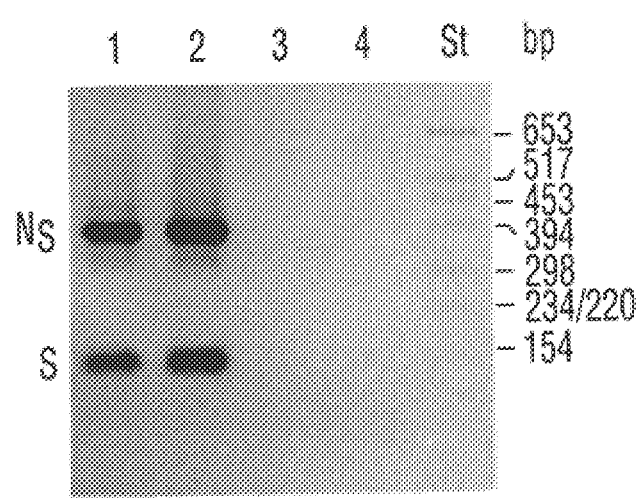
FIG. 7 shows an expression analysis of wbeI-uidA::nptII mRNA in stably transformed wheat cell lines; PCR products obtained from amplifications with BE28/GUS6 primers [SEQ ID NOS: 20 and 21] and cDNA derived from RNA of the cell lines GK105-1:2 (lane 1), GK107-12:1 (lane 2) and HY320 (lane 3) are shown; Lane 4 shows reaction with no template added; migration of molecular size marker (St) is shown to the right. Migration of amplified cDNA derived from non-spliced (NS) and spliced mRNA (S) is shown.

The promoter deletion analysis (FIG. 5) showed that the start site for P2 transcription must be located downstream of the EspI site at position 2249. A TATA-rich sequence (position 2401–2408) located 61 bp upstream of a possible translational start codon (position 2470–2472) was considered as a likely candidate as TATA-box for the P2 promoter. To verify that the P2 transcript originated upstream of position 2490, an RT-PCR experiment was performed with primers BE28 (5'-CTCTGCCTTTACGCGATCC-3')[SEQ ID NO:20] and GUS6 (5'-CGCGATCCAGACTGAATGC-3')[SEQ ID NO:21] and cDNA derived from the stably transformed cell lines GK105-1:2 and GK107-12:1 or untransformed HY320 cells (Table 2). The forward BE28 primer corresponded to wbeI sequences 2490–2508, whereas the reverse GUS6 primer annealed to region located 58 bp downstream of the start of the GUS coding sequence carried by pGK105 and pGK107. The RT-PCR reactions were assembled as described in Example 4 and the amplification was for 30 cycles of 1 min at 94° C., 45 sec at 60° C., 2 min at 72° C. followed by an extension step at 72° C. for 7 min. Gel analysis of the generated RT-PCR products revealed that cDNA derived from the GK105-1:2 and the GK107-12:1 cell lines produced in both cases two major products of 0.4 and 0.15 kb (FIG. 7, lanes 1 and 2). No RT-PCR product was obtained from cDNA of untransformed cells. The two fragments obtained from amplification with GK105-1:2 cDNA were isolated, cloned into a T-vector and DNA sequenced. The larger 386 bp RT-PCR product corresponded to an unspliced RNA or genomic DNA spanning the distance between the recognition sites for the PCR primers, whereas the smaller RT-PCR product corresponded to a wbeI-uidA transcript, in which the 2509–2751 region was absent. As a 0.15 kb RT-PCR product was also obtained with cDNA from cell line GK107-1:1, in which no P1 promoter is linked to the GUS gene strongly suggested that the 143 bp product represented a spliced P2 transcript where coding region IB was fused to coding region III (FIGS. 1 and 2). Splicing at these sites of the primary transcript are in agreement with the presence of typical splice donor and acceptor sequences. These data showed that the P2 transcript originated upstream of position 2490, leaving the TATA-rich sequence at position 1972 as the most likely TATA-box for the P2 promoter. Thus wbeI has the unusual feature of containing a promoter located within an intron of another transcribed region.

EXAMPLE 10

Effectiveness of promoters P1 and P2 in barley, oat and maize suspension cells

The plasmids pBE64-3 (containing the P1 and P2 promoters), pBE64-6 (containing only the P2 promoter) and pGUS14 (promoter-less vector) were tested by transient expression in barley, oat and maize cells, respectively (Table 3). Significant levels of GUS activity were observed in cells bombarded with pBE64-3 and pBE64-6, respectively, which demonstrated that the wbeI promoter is active in several monocots. As was also noted for transient expression in wheat cells (Example 7), the P2 promoter alone was two to four times more active than the P1, P2 combination. The Act1D-GUS construct expressed a three to six-fold higher level of GUS activity than pBE64-6 construct in all cell lines tested (data not shown).

TABLE 3

Transient expression of wbe1-promoter GUS fusions in different cereal cell lines.

| Cell Line | Construct | GUS specific activity nmol MU/h × mg protein* |
|---|---|---|
| Heartland (barley) | PBE64-3 | 26.0 ± 13.7 |
| | pBE64-6 | 54.3 ± 17.6 |
| | pGUS14 | 0.4 ± 0.4 |
| | — | 0.4 ± 0.2 |
| Black Mexican Sweet (maize) | pBE64-3 | 0.6 ± 0.3 |
| | pBE64-6 | 2.2 ± 0.9 |
| | pGUS14 | 0.1 ± 0.1 |
| | — | 0.1 ± 0.1 |
| S229-5 (oat) | pBE64-3 | 0.9 ± 0.4 |
| | pBE64-6 | 2.5 ± 0.6 |
| | PGUS14 | 0.1 ± 0.1 |
| | — | 0.2 ± 0.1 |

*The GUS activities were determined from at least three independent assays.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 2959 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Triticum aestivum
        ( B ) STRAIN: Biggar ( x i ) SEQUENCE DESCRIPTION: SEQ ID NO:1:

```
GTCGACGACC  CGATCGACGT  CCTGATGCGG  CTCTCCACCC  TCGAAGAGCG  CAACCAGGAG      60

CGCATCAGTC  GGGAGTTCTG  CCCTGCAACC  ATCGATGAGA  AGGAGTCGCG  GGAGCTTGCC     120

TCCACCTCTT  CCTCAACAAT  CTCTCGGAGG  AGGGGGGCTA  GAGGACGTCG  GAGGCAATAG     180

TACAACAAAT  AGTAGAACAT  AGGAATGTCG  AATAGCGACA  TCCCAAAAAT  GTCACTCAAC     240

GACATTTGAA  GTCGCAAAAA  ATGTAATACA  ACAGCTTTTG  GCCAGTAATA  TAAGGTTATC     300

ATGTTTGATG  ATGGTTTGAG  CTGGTTTGGT  TCAACTAAAT  GTACCTTAAA  CTTAACATAC     360

AAATTTGAAG  CAAATGAAAA  AAGGAACAAA  TAAAACTACA  AATATGGAGG  CGCATATAGA     420
```

```
GACTACGTGG  TTGTGCACAA  TCGCCACAGC  TATGGTGACC  GGAAATATGA  TGACTCTACT    480
AGAGTTGCTC  TAAGGCCGCT  TTTTGCGTCT  TCCACTTGTC  GTGCAGGGTT  GTCCCATGTA    540
GTTTTTTTTA  ACATAGTACA  TATGCAAGCA  CTCATATACA  CACGCATACA  CTCACATCTA    600
TGAATGCACA  TACGCACACC  GTATCCCTGT  GAGCACTAAA  GGCGAGCACG  GGACTTGAA     660
CCCTGGTGAG  CTAGGGAGAC  CACAGTCCTT  CTAACCATCC  AACCATTGGT  TGATTCGCGG    720
GAGCGATGGT  AGTTGGACTA  TTGGTTTTCT  CTCTCTCTCT  CTCTCTCTCT  CTCTCTTGGT    780
TGTTCCAGAT  TTATATATCC  TTTTTTCATT  CCCCCTTTTT  TTTCTTGTTT  TCTTCGAATT    840
TCATCCTTTC  CTAGTACTAA  TATGGAAATG  CACACACAAA  CATAGAAAGT  GTAAACACTA    900
ACGTGAGAAG  TATGTTTACA  CGGTAAAATA  ATTTAATCGA  AACATACCAA  TATGGGATAT    960
AGTTCTGAAT  ATATAGATAC  GACCAATGCA  ACCACTTCAA  ATTTTGAACG  CCCGATCTTA   1020
TTTTTTTTGA  GGAAGGTATA  TGATAAAACT  CCGATCTAGC  CCAACCACAT  GCTATAATCT   1080
TGTACCATAT  GAAACCACGT  CTGCTATTTT  GGCGGTTGCC  TCAAAACAAA  AGTAATGTTA   1140
TCCGGTTTCC  AACTCAAAGA  AAGAGAGTCA  GGTAGCGTGA  AGCTCCGAGG  CTGAGATGGG   1200
GACGAGCATG  GCGCCCCTAG  AGAGACCTCG  CCGTAGACGG  GGACATTGCG  GTTGACACGA   1260
GAGAAGTGAG  GGGGTTGCGA  GATGCGTGAG  ACAACACGTT  AGCAAAGTAG  GGAGAGGGTA   1320
GAAGAACTAA  GGGAGAAAGA  AGAGCAGTAG  CCGGCGAAAC  ATTGTACACC  ATTTTTTTTC   1380
CAGCGACCTA  GCGAATAGGC  AGGCCCTACA  AAATCTCGTT  TGGTTTTCCC  ACGCCGACAA   1440
GCTCCAACCA  GCCATACCAT  ACCATAGGCG  TCTCACATGT  CCTTCTAGTC  TTCGCAAAAA   1500
GTAATTATTT  TTGCCGGACA  ATGCAAGGAG  TGATATTTTT  ATATAGTTTT  CCTTCCTTTT   1560
TTTTGCGAAT  ACTATAGTTT  TCCTTCTTTA  GAAAAAGCAG  TCCTTCCATA  GTTTCTTTTG   1620
TGAAAGCAAT  GCCTTTTTAG  CGATTGGGAT  GTTCCTTTTT  AGAGCAAAAA  AAAACATCTT   1680
ACACTTTTTG  GCAAAACCGA  CGACGAAGGC  TGGAAAAAAG  AAGTGACGAA  GGCTGAAAGT   1740
GGCGAGACAC  GTGAGGGCCC  ATGGCTTCCG  TCCGGCCCAG  CGGCGCACGA  CCCCGGCCCG   1800
CCCGGGCCCA  CAGATCCGCT  TCTCCCTCGC  CCCCGTTTCC  CCCTCCCTCC  CTCTCGTTGC   1860
TTCCACTCCA  CTGTTCTCCT  CCCCTGTCCA  AAGCGGCCAC  GGACCGGAAA  AAATCACGGC   1920
TTTCCGTTGC  GTCTCCGGCG  CCACACTCCT  CCTCCTCCTC  CCTCCGGCCG  CTATAAAGCG   1980
CGCCGGGCCA  CGGGCCCCGC  GGACAATGGG  ATCCCGTCC   GCCGCCATCG  ACGAAGATGC   2040
TCTGCCTCAC  CGCCTCCTCC  TCGCCCTCGC  CCTCGCCCTC  TCTCCGCCG   CGCCCTCCC    2100
GTCCCGCTGC  TGACCGGCCC  GGACCGGGGA  TCTCGGTGAG  TCACTCGGGA  TCTTCATTTC   2160
TTTTCTTTTC  TTTCGTTTCC  GGCCTCCGTT  CTGCCAGCCG  GAGGTTCCCT  GATGCGATGC   2220
CGCGCGCGCA  GGGCGGCGGC  AATGTGCGGC  TGAGCGCGGT  GCCCGCGCCG  TCTTCGCTTC   2280
GCTGGTCGTG  GCCGCGGAAG  GTGAGCCCTC  TCCCTGTCT   ACCCAGATTT  GCGACCCTGA   2340
TCCCCTGTTG  TCGCCGGGCA  AACTGAATCT  GATCCACGCT  GGTTATTGGA  AATACTGTAG   2400
TATATATACT  ACTAATAAAC  CTGAGGCTGG  GATTCGTCCA  CCTGACGCCG  TCCACTGAGG   2460
AACAAGTGGA  TGCGATTTCG  ATTGAATTTC  TCTGCCTTTA  CGCGATCCGT  ACGCACAATA   2520
TCCCCTCCTG  CGGTATCTCA  ACCGTATTAC  TTTCTGCACA  ACCCAAATGC  GTATAATCTT   2580
TGCTGAATCT  ATCAACCAAT  AATCTGTGAT  GAATATATCA  ACCAAATTAG  TTGCTGCATT   2640
GTGACAAATA  TATTTAATTG  ATATAGGCAA  ATGTTCATGT  GCTGTATCTC  CATTACTTCT   2700
TTAGTTGTTG  TAAATCTGCC  GCTCGCTCTA  ACTGTCGTTC  ATTTTTGGAA  GGCCAAGAGC   2760
AAGTTCTCTG  TTCCCGTGTC  TGCGCCAAGA  GACTACACCA  TGGCAACAGC  TGAAGATGGC   2820
```

```
TTCGGCGACC  TTCCGATATA  CGATCTGGAT  CCCAAGTTCG  CCGGCTTCAA  GGACCACTTC      2880

AGTTACAGGA  TGAAAAGTA   TCTTGAACAG  AAACATTCGA  TCGAGAAATA  CGAGGGGGGC      2940

CTTGAAGAGT  TCTCTAAAG                                                      2959
```

(2) INFORMATION FOR SEQ ID NO:2:

(i) SEQUENCE CHARACTERISTICS:
        (A) LENGTH: 125 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Triticum aestivum
        (B) STRAIN: Biggar (xi) SEQUENCE DESCRIPTION: SEQ ID NO:2:

```
Met  Leu  Cys  Leu  Thr  Ala  Ser  Ser  Ser  Pro  Ser  Pro  Ser  Pro  Ser  Leu
1                   5                        10                       15

Pro  Pro  Arg  Pro  Ser  Arg  Pro  Ala  Ala  Asp  Arg  Pro  Gly  Pro  Gly  Ile
               20                       25                       30

Ser  Gly  Gly  Gly  Asn  Val  Arg  Leu  Ser  Ala  Val  Pro  Ala  Pro  Ser  Ser
          35                        40                       45

Leu  Arg  Trp  Ser  Trp  Pro  Arg  Lys  Ala  Lys  Ser  Lys  Phe  Ser  Val  Pro
     50                        55                       60

Val  Ser  Ala  Pro  Arg  Asp  Tyr  Thr  Met  Ala  Thr  Ala  Glu  Asp  Gly  Phe
65                       70                       75                       80

Gly  Asp  Leu  Pro  Ile  Tyr  Asp  Leu  Asp  Pro  Lys  Phe  Ala  Gly  Phe  Lys
                    85                       90                       95

Asp  His  Phe  Ser  Tyr  Arg  Met  Lys  Lys  Tyr  Leu  Glu  Gln  Lys  His  Ser
               100                      105                      110

Ile  Glu  Lys  Tyr  Glu  Gly  Gly  Leu  Glu  Glu  Phe  Ser  Lys
          115                      120                      125
```

(2) INFORMATION FOR SEQ ID NO:3:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Triticum aestivum
        (B) STRAIN: Biggar (xi) SEQUENCE DESCRIPTION: SEQ ID NO:3:

```
CCGCGGACAA  TGGGATCCCC  GTCCGCCGCC  ATCGACGAAG  ATGCTCTGCC  TCACCGCCTC        60

CTCCTCGCCC  TCGCCCTCGC  CCTCTCTCCC  GCCGCGCCCC  TCCCGTCCCG  CTGCTGACCG       120

GCCCGGACCG  GGGATCTCGG  TGAGTCACTC  GGGATCTTCA  TTTCTTTTCT  TTTCTTTCGT       180
```

| | | | | | | |
|---|---|---|---|---|---|---|
| TTCCGGCCTC | CGTTCTGCCA | GCCGGAGGTT | CCCTGATGCG | ATGCCGCGCG | CGCAGGGCGG | 240 |
| CGGCAATGTG | CGGCTGAGCG | CGGTGCCCGC | GCCGTCTTCG | CTTCGCTGGT | CGTGGCCGCG | 300 |
| GAAGGTGAGC | CCTCTCCCCT | GTCTACCCAG | ATTTGCGACC | CTGATCCCCT | GTTGTCGCCG | 360 |
| GGCAAACTGA | ATCTGATCCA | CGCTGGTTAT | TGGAAATACT | GTAGTATATA | TACTACTAAT | 420 |
| AAACCTGAGG | CTGGGATTCG | TCCACCTGAC | GCCGTCCACT | GAGGAACAAG | TGGATGCGAT | 480 |
| TTCGATTGAA | TTTCTCTGCC | TTTACGCGAT | CCGTACGCAC | AATATCCCCT | CCTGCGGTAT | 540 |
| CTCAACCGTA | TTACTTTCTG | CACAACCCAA | ATGCGTATAA | TCTTTGCTGA | ATCTATCAAC | 600 |
| CAATAATCTG | TGATGAATAT | ATCAACCAAA | TTAGTTGCTG | CATTGTGACA | AATATATTTA | 660 |
| ATTGATATAG | GCAAATGTTC | ATGTGCTGTA | TCTCCATTAC | TTCTTTAGTT | GTTGTAAATC | 720 |
| TGCCGCTCGC | TCTAACTGTC | GTTCATTTTT | GGAAGGCCAA | GAGCAAGTTC | TCTGTTCCCG | 780 |
| TGTCTGCGCC | AAGAGACTAC | ACCATGG | | | | 807 |

( 2 ) INFORMATION FOR SEQ ID NO:4:

( i ) SEQUENCE CHARACTERISTICS:
        ( A ) LENGTH: 553 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Triticum aestivum
        ( B ) STRAIN: Biggar ( x i ) SEQUENCE DESCRIPTION: SEQ ID NO:4:

| | | | | | | |
|---|---|---|---|---|---|---|
| TGAGCGCGGT | GCCCGCGCCG | TCTTCGCTTC | GCTGGTCGTG | GCCGCGGAAG | GTGAGCCCTC | 60 |
| TCCCCTGTCT | ACCCAGATTT | GCGACCCTGA | TCCCCTGTTG | TCGCCGGGCA | AACTGAATCT | 120 |
| GATCCACGCT | GGTTATTGGA | AATACTGTAG | TATATATACT | ACTAATAAAC | CTGAGGCTGG | 180 |
| GATTCGTCCA | CCTGACGCCG | TCCACTGAGG | AACAAGTGGA | TGCGATTTCG | ATTGAATTTC | 240 |
| TCTGCCTTTA | CGCGATCCGT | ACGCACAATA | TCCCCTCCTG | CGGTATCTCA | ACCGTATTAC | 300 |
| TTTCTGCACA | ACCCAAATGC | GTATAATCTT | TGCTGAATCT | ATCAACCAAT | AATCTGTGAT | 360 |
| GAATATATCA | ACCAAATTAG | TTGCTGCATT | GTGACAAATA | TATTTAATTG | ATATAGGCAA | 420 |
| ATGTTCATGT | GCTGTATCTC | CATTACTTCT | TTAGTTGTTG | TAAATCTGCC | GCTCGCTCTA | 480 |
| ACTGTCGTTC | ATTTTTGGAA | GGCCAAGAGC | AAGTTCTCTG | TTCCCGTGTC | TGCGCCAAGA | 540 |
| GACTACACCA | TGG | | | | | 553 |

( 2 ) INFORMATION FOR SEQ ID NO:5:

( i ) SEQUENCE CHARACTERISTICS:
        ( A ) LENGTH: 790 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Triticum aestivum
(B) STRAIN: Biggar (xi) SEQUENCE DESCRIPTION: SEQ ID NO:5:

```
GGATCCCCGT CCGCCGCCAT CGACGAAGAT GCTCTGCCTC ACCGCCTCCT CCTCGCCCTC      60
GCCCTCGCCC TCTCTCCCGC CGCGCCCCTC CCGTCCCGCT GCTGACCGGC CCGGACCGGG     120
GATCTCGGTG AGTCACTCGG GATCTTCATT TCTTTTCTTT TCTTTCGTTT CCGGCCTCCG     180
TTCTGCCAGC CGGAGGTTCC CTGATGCGAT GCCGCGCGCG CAGGGCGGCG GCAATGTGCG     240
GCTGAGCGCG GTGCCCGCGC CGTCTTCGCT TCGCTGGTCG TGGCCGCGGA AGGTGAGCCC     300
TCTCCCCTGT CTACCCAGAT TTGCGACCCT GATCCCTGT  TGTCGCCGGG CAAACTGAAT     360
CTGATCCACG CTGGTTATTG GAAATACTGT AGTATATATA CTACTAATAA ACCTGAGGCT     420
GGGATTCGTC CACCTGACGC CGTCCACTGA GGAACAAGTG GATGCGATTT CGATTGAATT     480
TCTCTGCCTT TACGCGATCC GTACGCACAA TATCCCCTCC TGCGGTATCT CAACCGTATT     540
ACTTTCTGCA CAACCCAAAT GCGTATAATC TTTGCTGAAT CTATCAACCA ATAATCTGTG     600
ATGAATATAT CAACCAAATT AGTTGCTGCA TTGTGACAAA TATATTTAAT TGATATAGGC     660
AAATGTTCAT GTGCTGTATC TCCATTACTT CTTTAGTTGT TGTAAATCTG CCGCTCGCTC     720
TAACTGTCGT TCATTTTTGG AAGGCCAAGA GCAAGTTCTC TGTTCCCGTG TCTGCGCCAA     780
GAGACTACAC                                                            790
```

(2) INFORMATION FOR SEQ ID NO:6:

(i) SEQUENCE CHARACTERISTICS:
(A) LENGTH: 799 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Triticum aestivum
(B) STRAIN: Biggar (xi) SEQUENCE DESCRIPTION: SEQ ID NO:6:

```
GGATCCCCGT CCGCCGCCAT CGACGAAGAT GCTCTGCCTC ACCGCCTCCT CCTCGCCCTC      60
GCCCTCGCCC TCTCTCCCGC CGCGCCCCTC CCGTCCCGCT GCTGACCGGC CCGGACCGGG     120
GATCTCGGTG AGTCACTCGG GATCTTCATT TCTTTTCTTT TCTTTCGTTT CCGGCCTCCG     180
TTCTGCCAGC CGGAGGTTCC CTGATGCGAT GCCGCGCGCG CAGGGCGGCG GCAATGTGCG     240
GCTGAGCGCG GTGCCCGCGC CGTCTTCGCT TCGCTGGTCG TGGCCGCGGA AGGTGAGCCC     300
TCTCCCCTGT CTACCCAGAT TTGCGACCCT GATCCCTGT  TGTCGCCGGG CAAACTGAAT     360
CTGATCCACG CTGGTTATTG GAAATACTGT AGTATATATA CTACTAATAA ACCTGAGGCT     420
GGGATTCGTC CACCTGACGC CGTCCACTGA GGAACAAGTG GATGCGATTT CGATTGAATT     480
TCTCTGCCTT TACGCGATCC GTACGCACAA TATCCCCTCC TGCGGTATCT CAACCGTATT     540
ACTTTCTGCA CAACCCAAAT GCGTATAATC TTTGCTGAAT CTATCAACCA ATAATCTGTG     600
ATGAATATAT CAACCAAATT AGTTGCTGCA TTGTGACAAA TATATTTAAT TGATATAGGC     660
AAATGTTCAT GTGCTGTATC TCCATTACTT CTTTAGTTGT TGTAAATCTG CCGCTCGCTC     720
TAACTGTCGT TCATTTTTGG AAGGCCAAGA GCAAGTTCTC TGTTCCCGTG TCTGCGCCAA     780
```

| GAGACTACAC CATGGCAAC | 799 |

(2) INFORMATION FOR SEQ ID NO:7:

(i) SEQUENCE CHARACTERISTICS:
        (A) LENGTH: 2807 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Triticum aestivum
        (B) STRAIN: Biggar (xi) SEQUENCE DESCRIPTION: SEQ ID NO:7:

| GTCGACGACC | CGATCGACGT | CCTGATGCGG | CTCTCCACCC | TCGAAGAGCG | CAACCAGGAG | 60 |
| CGCATCAGTC | GGGAGTTCTG | CCCTGCAACC | ATCGATGAGA | AGGAGTCGCG | GGAGCTTGCC | 120 |
| TCCACCTCTT | CCTCAACAAT | CTCTCGGAGG | AGGGGGGCTA | GAGGACGTCG | GAGGCAATAG | 180 |
| TACAACAAAT | AGTAGAACAT | AGGAATGTCG | AATAGCGACA | TCCCAAAAAT | GTCACTCAAC | 240 |
| GACATTTGAA | GTCGCAAAAA | ATGTAATACA | ACAGCTTTTG | GCCAGTAATA | TAAGGTTATC | 300 |
| ATGTTTGATG | ATGGTTTGAG | CTGGTTTGGT | TCAACTAAAT | GTACCTTAAA | CTTAACATAC | 360 |
| AAATTTGAAG | CAAATGAAAA | AAGGAACAAA | TAAAACTACA | AATATGGAGG | CGCATATAGA | 420 |
| GACTACGTGG | TTGTGCACAA | TCGCCACAGC | TATGGTGACC | GGAAATATGA | TGACTCTACT | 480 |
| AGAGTTGCTC | TAAGGCCGCT | TTTTGCGTCT | TCCACTTGTC | GTGCAGGGTT | GTCCCATGTA | 540 |
| GTTTTTTTTA | ACATAGTACA | TATGCAAGCA | CTCATATACA | CACGCATACA | CTCACATCTA | 600 |
| TGAATGCACA | TACGCACACC | GTATCCCTGT | GAGCACTAAA | GGCGAGCACG | GGGACTTGAA | 660 |
| CCCTGGTGAG | CTAGGGAGAC | CACAGTCCTT | CTAACCATCC | AACCATTGGT | TGATTCGCGG | 720 |
| GAGCGATGGT | AGTTGGACTA | TTGGTTTTCT | CTCTCTCTCT | CTCTCTCTCT | CTCTCTTGGT | 780 |
| TGTTCCAGAT | TTATATATCC | TTTTTTCATT | CCCCTTTTT | TTTCTTGTTT | TCTTCGAATT | 840 |
| TCATCCTTTC | CTAGTACTAA | TATGGAAATG | CACACACAAA | CATAGAAAGT | GTAAACACTA | 900 |
| ACGTGAGAAG | TATGTTTACA | CGGTAAAATA | ATTTAATCGA | AACATACCAA | TATGGGATAT | 960 |
| AGTTCTGAAT | ATATAGATAC | GACCAATGCA | ACCACTTCAA | ATTTTGAACG | CCCGATCTTA | 1020 |
| TTTTTTTTGA | GGAAGGTATA | TGATAAAACT | CCGATCTAGC | CCAACCACAT | GCTATAATCT | 1080 |
| TGTACCATAT | GAAACCACGT | CTGCTATTTT | GGCGGTTGCC | TCAAAACAAA | AGTAATGTTA | 1140 |
| TCCGGTTTCC | AACTCAAAGA | AAGAGAGTCA | GGTAGCGTGA | AGCTCCGAGG | CTGAGATGGG | 1200 |
| GACGAGCATG | GCGCCCCTAG | AGAGACCTCG | CCGTAGACGG | GGACATTGCG | GTTGACACGA | 1260 |
| GAGAAGTGAG | GGGGTTGCGA | GATGCGTGAG | ACAACACGTT | AGCAAAGTAG | GGAGAGGGTA | 1320 |
| GAAGAACTAA | GGGAGAAAGA | AGAGCAGTAG | CCGGCGAAAC | ATTGTACACC | ATTTTTTTTC | 1380 |
| CAGCGACCTA | GCGAATAGGC | AGGCCCTACA | AAATCTCGTT | TGGTTTTCCC | ACGCCGACAA | 1440 |
| GCTCCAACCA | GCCATACCAT | ACCATAGGCG | TCTCACATGT | CCTTCTAGTC | TTCGCAAAAA | 1500 |
| GTAATTATTT | TTGCCGGACA | ATGCAAGGAG | TGATATTTTT | ATATAGTTTT | CCTTCCTTTT | 1560 |
| TTTTGCGAAT | ACTATAGTTT | TCCTTCTTTA | GAAAAGCAG | TCCTTCCATA | GTTTCTTTTG | 1620 |
| TGAAAGCAAT | GCCTTTTTAG | CGATTGGGAT | GTTCCTTTTT | AGAGCAAAAA | AAAACATCTT | 1680 |
| ACACTTTTTG | GCAAAACCGA | CGACGAAGGC | TGGAAAAAAG | AAGTGACGAA | GGCTGAAAGT | 1740 |

| | | | | | | |
|---|---|---|---|---|---|---|
| GGCGAGACAC | GTGAGGGCCC | ATGGCTTCCG | TCCGGCCCAG | CGGCGCACGA | CCCCGGCCCG | 1800 |
| CCCGGGCCCA | CAGATCCGCT | TCTCCCTCGC | CCCCGTTTCC | CCCTCCCTCC | CTCTCGTTGC | 1860 |
| TTCCACTCCA | CTGTTCTCCT | CCCCTGTCCA | AAGCGGCCAC | GGACCGGAAA | AAATCACGGC | 1920 |
| TTTCCGTTGC | GTCTCCGGCG | CCACACTCCT | CCTCCTCCTC | CCTCCGGCCG | CTATAAAGCG | 1980 |
| CGCCGGGCCA | CGGGCCCCGC | GGACAATGGG | ATCCCCGTCC | GCCGCCATCG | ACGAAGATGC | 2040 |
| TCTGCCTCAC | CGCCTCCTCC | TCGCCCTCGC | CCTCGCCCTC | TCTCCCGCCG | CGCCCCTCCC | 2100 |
| GTCCCGCTGC | TGACCGGCCC | GGACCGGGGA | TCTCGGTGAG | TCACTCGGGA | TCTTCATTTC | 2160 |
| TTTTCTTTTC | TTTCGTTTCC | GGCCTCCGTT | CTGCCAGCCG | GAGGTTCCCT | GATGCGATGC | 2220 |
| CGCGCGCGCA | GGGCGGCGGC | AATGTGCGGC | TGAGCGCGGT | GCCCGCGCCG | TCTTCGCTTC | 2280 |
| GCTGGTCGTG | GCCGCGGAAG | GTGAGCCCTC | TCCCTGTCT | ACCCAGATTT | GCGACCCTGA | 2340 |
| TCCCCTGTTG | TCGCCGGGCA | AACTGAATCT | GATCCACGCT | GGTTATTGGA | AATACTGTAG | 2400 |
| TATATATACT | ACTAATAAAC | CTGAGGCTGG | GATTCGTCCA | CCTGACGCCG | TCCACTGAGG | 2460 |
| AACAAGTGGA | TGCGATTTCG | ATTGAATTTC | TCTGCCTTTA | CGCGATCCGT | ACGCACAATA | 2520 |
| TCCCCTCCTG | CGGTATCTCA | ACCGTATTAC | TTTCTGCACA | ACCCAAATGC | GTATAATCTT | 2580 |
| TGCTGAATCT | ATCAACCAAT | AATCTGTGAT | GAATATATCA | ACCAAATTAG | TTGCTGCATT | 2640 |
| GTGACAAATA | TATTTAATTG | ATATAGGCAA | ATGTTCATGT | GCTGTATCTC | CATTACTTCT | 2700 |
| TTAGTTGTTG | TAAATCTGCC | GCTCGCTCTA | ACTGTCGTTC | ATTTTGGAA | GGCCAAGAGC | 2760 |
| AAGTTCTCTG | TTCCCGTGTC | TGCGCCAAGA | GACTACACCA | TGGCAAC | | 2807 |

(2) INFORMATION FOR SEQ ID NO:8:

(i) SEQUENCE CHARACTERISTICS:
        (A) LENGTH: 2803 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Triticum aestivum
        (B) STRAIN: Biggar (xi) SEQUENCE DESCRIPTION: SEQ ID NO:8:

| | | | | | | |
|---|---|---|---|---|---|---|
| GTCGACGACC | CGATCGACGT | CCTGATGCGG | CTCTCCACCC | TCGAAGAGCG | CAACCAGGAG | 60 |
| CGCATCAGTC | GGGAGTTCTG | CCCTGCAACC | ATCGATGAGA | AGGAGTCGCG | GGAGCTTGCC | 120 |
| TCCACCTCTT | CCTCAACAAT | CTCTCGGAGG | AGGGGGGCTA | GAGGACGTCG | GAGGCAATAG | 180 |
| TACAACAAAT | AGTAGAACAT | AGGAATGTCG | AATAGCGACA | TCCCAAAAAT | GTCACTCAAC | 240 |
| GACATTTGAA | GTCGCAAAAA | ATGTAATACA | ACAGCTTTTG | GCCAGTAATA | TAAGGTTATC | 300 |
| ATGTTTGATG | ATGGTTTGAG | CTGGTTTGGT | TCAACTAAAT | GTACCTAAAA | CTTAACATAC | 360 |
| AAATTTGAAG | CAAATGAAAA | AAGGAACAAA | TAAAACTACA | AATATGGAGG | CGCATATAGA | 420 |
| GACTACGTGG | TTGTGCACAA | TCGCCACAGC | TATGGTGACC | GGAAATATGA | TGACTCTACT | 480 |
| AGAGTTGCTC | TAAGGCCGCT | TTTTGCGTCT | TCCACTTGTC | GTGCAGGGTT | GTCCCATGTA | 540 |
| GTTTTTTTTA | ACATAGTACA | TATGCAAGCA | CTCATATACA | CACGCATACA | CTCACATCTA | 600 |
| TGAATGCACA | TACGCACACC | GTATCCCTGT | GAGCACTAAA | GGCGAGCACG | GGGACTTGAA | 660 |

| | | | | | | |
|---|---|---|---|---|---|---|
| CCCTGGTGAG | CTAGGGAGAC | CACAGTCCTT | CTAACCATCC | AACCATTGGT | TGATTCGCGG | 720 |
| GAGCGATGGT | AGTTGGACTA | TTGGTTTTCT | CTCTCTCTCT | CTCTCTCTCT | CTCTCTTGGT | 780 |
| TGTTCCAGAT | TTATATATCC | TTTTTTCATT | CCCCCTTTTT | TTTCTTGTTT | TCTTCGAATT | 840 |
| TCATCCTTTC | CTAGTACTAA | TATGGAAATG | CACACACAAA | CATAGAAAGT | GTAAACACTA | 900 |
| ACGTGAGAAG | TATGTTTACA | CGGTAAAATA | ATTAATCGA | AACATACCAA | TATGGGATAT | 960 |
| AGTTCTGAAT | ATATAGATAC | GACCAATGCA | ACCACTTCAA | ATTTTGAACG | CCCGATCTTA | 1020 |
| TTTTTTTTGA | GGAAGGTATA | TGATAAAACT | CCGATCTAGC | CCAACCACAT | GCTATAATCT | 1080 |
| TGTACCATAT | GAAACCACGT | CTGCTATTTT | GGCGGTTGCC | TCAAAACAAA | AGTAATGTTA | 1140 |
| TCCGGTTTCC | AACTCAAAGA | AAGAGAGTCA | GGTAGCGTGA | AGCTCCGAGG | CTGAGATGGG | 1200 |
| GACGAGCATG | GCGCCCCTAG | AGAGACCTCG | CCGTAGACGG | GGACATTGCG | GTTGACACGA | 1260 |
| GAGAAGTGAG | GGGGTTGCGA | GATGCGTGAG | ACAACACGTT | AGCAAAGTAG | GGAGAGGGTA | 1320 |
| GAAGAACTAA | GGGAGAAAGA | AGAGCAGTAG | CCGGCGAAAC | ATTGTACACC | ATTTTTTTC | 1380 |
| CAGCGACCTA | GCGAATAGGC | AGGCCCTACA | AAATCTCGTT | TGGTTTTCCC | ACGCCGACAA | 1440 |
| GCTCCAACCA | GCCATACCAT | ACCATAGGCG | TCTCACATGT | CCTTCTAGTC | TTCGCAAAAA | 1500 |
| GTAATTATTT | TTGCCGGACA | ATGCAAGGAG | TGATATTTTT | ATATAGTTTT | CCTTCCTTTT | 1560 |
| TTTTGCGAAT | ACTATAGTTT | TCCTTCTTTA | GAAAAAGCAG | TCCTTCCATA | GTTTCTTTTG | 1620 |
| TGAAAGCAAT | GCCTTTTTAG | CGATTGGGAT | GTTCCTTTTT | AGAGCAAAAA | AAAACATCTT | 1680 |
| ACACTTTTTG | GCAAAACCGA | CGACGAAGGC | TGGAAAAAAG | AAGTGACGAA | GGCTGAAAGT | 1740 |
| GGCGAGACAC | GTGAGGGCCC | ATGGCTTCCG | TCCGGCCCAG | CGGCGCACGA | CCCCGGCCCG | 1800 |
| CCCGGGCCCA | CAGATCCGCT | TCTCCCTCGC | CCCCGTTTCC | CCCTCCCTCC | CTCTCGTTGC | 1860 |
| TTCCACTCCA | CTGTTCTCCT | CCCCTGTCCA | AAGCGGCCAC | GGACCGGAAA | AAATCACGGC | 1920 |
| TTTCCGTTGC | GTCTCCGGCG | CCACACTCCT | CCTCCTCCTC | CCTCCGGCCG | CTATAAGCG | 1980 |
| CGCCGGGCCA | CGGGCCCCGC | GGACAATGGG | ATCCCCGTCC | GCCGCCATCG | ACGAAGATGC | 2040 |
| TCTGCCTCAC | CGCCTCCTCC | TCGCCCTCGC | CCTCGCCCTC | TCTCCCGCCG | CGCCCCTCCC | 2100 |
| GTCCCGCTGC | TGACCGGCCC | GGACCGGGGA | TCTCGGTGAG | TCACTCGGGA | TCTTCATTTC | 2160 |
| TTTTCTTTTC | TTTCGTTTCC | GGCCTCCGTT | CTGCCAGCCG | GAGGTTCCCT | GATGCGATGC | 2220 |
| CGCGCGCGCA | GGGCGGCGGC | AATGTGCGGC | TGAGCGCGGT | GCCCGCGCCG | TCTTCGCTTC | 2280 |
| GCTGGTCGTG | GCCGCGGAAG | GTGAGCCCTC | TCCCCTGTCT | ACCCAGATTT | GCGACCCTGA | 2340 |
| TCCCCTGTTG | TCGCCGGGCA | AACTGAATCT | GATCCACGCT | GGTTATTGGA | AATACTGTAG | 2400 |
| TATATATACT | ACTAATAAAC | CTGAGGCTGG | GATTCGTCCA | CCTGACGCCG | TCCACTGAGG | 2460 |
| AACAAGTGGA | TGCGATTTCG | ATTGAATTTC | TCTGCCTTTA | CGCGATCCGT | ACGCACAATA | 2520 |
| TCCCCTCCTG | CGGTATCTCA | ACCGTATTAC | TTTCTGCACA | ACCCAAATGC | GTATAATCTT | 2580 |
| TGCTGAATCT | ATCAACCAAT | AATCTGTGAT | GAATATATCA | ACCAAATTAG | TTGCTGCATT | 2640 |
| GTGACAAATA | TATTTAATTG | ATATAGGCAA | ATGTTCATGT | GCTGTATCTC | CATTACTTCT | 2700 |
| TTAGTTGTTG | TAAATCTGCC | GCTCGCTCTA | ACTGTCGTTC | ATTTTTGGAA | GGCCAAGAGC | 2760 |
| AAGTTCTCTG | TTCCCGTGTC | TGCGCCAAGA | GACTACACCA | TGG | | 2803 |

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GAGACTACAC CATGGCAACA G     21

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

TCCATGATTG CCATCAGC     18

( 2 ) INFORMATION FOR SEQ ID NO:11:

( i ) SEQUENCE CHARACTERISTICS:
        ( A ) LENGTH: 2013 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Triticum aestivum
        ( B ) STRAIN: Biggar ( x i ) SEQUENCE DESCRIPTION: SEQ ID NO:11:

```
GTCGACGACC CGATCGACGT CCTGATGCGG CTCTCCACCC TCGAAGAGCG CAACCAGGAG      60
CGCATCAGTC GGGAGTTCTG CCCTGCAACC ATCGATGAGA AGGAGTCGCG GGAGCTTGCC     120
TCCACCTCTT CCTCAACAAT CTCTCGGAGG AGGGGGGCTA GAGGACGTCG GAGGCAATAG     180
TACAACAAAT AGTAGAACAT AGGAATGTCG AATAGCGACA TCCCAAAAAT GTCACTCAAC     240
GACATTTGAA GTCGCAAAAA ATGTAATACA ACAGCTTTTG GCCAGTAATA TAAGGTTATC     300
ATGTTTGATG ATGGTTTGAG CTGGTTTGGT TCAACTAAAT GTACCTTAAA CTTAACATAC     360
AAATTTGAAG CAAATGAAAA AAGGAACAAA TAAAACTACA AATATGGAGG CGCATATAGA     420
GACTACGTGG TTGTGCACAA TCGCCACAGC TATGGTGACC GGAAATATGA TGACTCTACT     480
AGAGTTGCTC TAAGGCCGCT TTTTGCGTCT TCCACTTGTC GTGCAGGGTT GTCCCATGTA     540
GTTTTTTTTA ACATAGTACA TATGCAAGCA CTCATATACA CACGCATACA CTCACATCTA     600
TGAATGCACA TACGCACACC GTATCCCTGT GAGCACTAAA GGCGAGCACG GGGACTTGAA     660
CCCTGGTGAG CTAGGGAGAC CACAGTCCTT CTAACCATCC AACCATTGGT TGATTCGCGG     720
GAGCGATGGT AGTTGGACTA TTGGTTTTCT CTCTCTCTCT CTCTCTCTCT CTCTCTTGGT     780
TGTTCCAGAT TTATATATCC TTTTTTCATT CCCCCTTTTT TTTCTTGTTT TCTTCGAATT     840
TCATCCTTTC CTAGTACTAA TATGGAAATG CACACACAAA CATAGAAAGT GTAAACACTA     900
```

| | | | | | | |
|---|---|---|---|---|---|---|
|ACGTGAGAAG|TATGTTTACA|CGGTAAAATA|ATTTAATCGA|AACATACCAA|TATGGGATAT|960|
|AGTTCTGAAT|ATATAGATAC|GACCAATGCA|ACCACTTCAA|ATTTTGAACG|CCCGATCTTA|1020|
|TTTTTTTTGA|GGAAGGTATA|TGATAAAACT|CCGATCTAGC|CCAACCACAT|GCTATAATCT|1080|
|TGTACCATAT|GAAACCACGT|CTGCTATTTT|GGCGGTTGCC|TCAAAACAAA|AGTAATGTTA|1140|
|TCCGGTTTCC|AACTCAAAGA|AAGAGAGTCA|GGTAGCGTGA|AGCTCCGAGG|CTGAGATGGG|1200|
|GACGAGCATG|GCGCCCCTAG|AGAGACCTCG|CCGTAGACGG|GGACATTGCG|GTTGACACGA|1260|
|GAGAAGTGAG|GGGGTTGCGA|GATGCGTGAG|ACAACACGTT|AGCAAGTAG|GGAGAGGGTA|1320|
|GAAGAACTAA|GGGAGAAAGA|AGAGCAGTAG|CCGGCGAAAC|ATTGTACACC|ATTTTTTTTC|1380|
|CAGCGACCTA|GCGAATAGGC|AGGCCCTACA|AAATCTCGTT|TGGTTTTCCC|ACGCCGACAA|1440|
|GCTCCAACCA|GCCATACCAT|ACCATAGGCG|TCTCACATGT|CCTTCTAGTC|TTCGCAAAAA|1500|
|GTAATTATTT|TTGCCGGACA|ATGCAAGGAG|TGATATTTTT|ATATAGTTTT|CCTTCCTTTT|1560|
|TTTTGCGAAT|ACTATAGTTT|TCCTTCTTTA|GAAAAGCAG|TCCTTCCATA|GTTTCTTTTG|1620|
|TGAAAGCAAT|GCCTTTTAG|CGATTGGGAT|GTTCCTTTTT|AGAGCAAAAA|AAAACATCTT|1680|
|ACACTTTTTG|GCAAAACCGA|CGACGAAGGC|TGGAAAAAG|AAGTGACGAA|GGCTGAAAGT|1740|
|GGCGAGACAC|GTGAGGGCCC|ATGGCTTCCG|TCCGGCCCAG|CGGCGCACGA|CCCCGGCCCG|1800|
|CCCGGGCCCA|CAGATCCGCT|TCTCCCTCGC|CCCCGTTTCC|CCCTCCCTCC|CTCTCGTTGC|1860|
|TTCCACTCCA|CTGTTCTCCT|CCCCTGTCCA|AAGCGGCCAC|GGACCGGAAA|AAATCACGGC|1920|
|TTTCCGTTGC|GTCTCCGGCG|CCACACTCCT|CCTCCTCCTC|CCTCCGGCCG|CTATAAAGCG|1980|
|CGCCGGGCCA|CGGGCCCCGC|GGACAATGGG|ATC| | |2013|

(2) INFORMATION FOR SEQ ID NO:12:

(i) SEQUENCE CHARACTERISTICS:
        (A) LENGTH: 2253 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Triticum aestivum
        (B) STRAIN: Biggar (xi) SEQUENCE DESCRIPTION: SEQ ID NO:12:

| | | | | | | |
|---|---|---|---|---|---|---|
|GTCGACGACC|CGATCGACGT|CCTGATGCGG|CTCTCCACCC|TCGAAGAGCG|CAACCAGGAG|60|
|CGCATCAGTC|GGGAGTTCTG|CCCTGCAACC|ATCGATGAGA|AGGAGTCGCG|GGAGCTTGCC|120|
|TCCACCTCTT|CCTCAACAAT|CTCTCGGAGG|AGGGGGCTA|GAGGACGTCG|GAGGCAATAG|180|
|TACAACAAAT|AGTAGAACAT|AGGAATGTCG|AATAGCGACA|TCCCAAAAAT|GTCACTCAAC|240|
|GACATTTGAA|GTCGCAAAAA|ATGTAATACA|ACAGCTTTTG|GCCAGTAATA|TAAGGTTATC|300|
|ATGTTTGATG|ATGGTTTGAG|CTGGTTTGGT|TCAACTAAAT|GTACCTTAAA|CTTAACATAC|360|
|AAATTTGAAG|CAAATGAAAA|AAGGAACAAA|TAAAACTACA|AATATGGAGG|CGCATATAGA|420|
|GACTACGTGG|TTGTGCACAA|TCGCCACAGC|TATGGTGACC|GGAAATATGA|TGACTCTACT|480|
|AGAGTTGCTC|TAAGGCCGCT|TTTTGCGTCT|TCCACTTGTC|GTGCAGGGTT|GTCCATGTA|540|
|GTTTTTTTA|ACATAGTACA|TATGCAAGCA|CTCATATACA|CACGCATACA|CTCACATCTA|600|

| | | | | | | |
|---|---|---|---|---|---|---|
| TGAATGCACA | TACGCACACC | GTATCCCTGT | GAGCACTAAA | GGCGAGCACG | GGGACTTGAA | 660 |
| CCCTGGTGAG | CTAGGGAGAC | CACAGTCCTT | CTAACCATCC | AACCATTGGT | TGATTCGCGG | 720 |
| GAGCGATGGT | AGTTGGACTA | TTGGTTTTCT | CTCTCTCTCT | CTCTCTCTCT | CTCTCTTGGT | 780 |
| TGTTCCAGAT | TTATATATCC | TTTTTTCATT | CCCCCTTTTT | TTTCTTGTTT | TCTTCGAATT | 840 |
| TCATCCTTTC | CTAGTACTAA | TATGGAAATG | CACACACAAA | CATAGAAAGT | GTAAACACTA | 900 |
| ACGTGAGAAG | TATGTTTACA | CGGTAAAATA | ATTTAATCGA | AACATACCAA | TATGGGATAT | 960 |
| AGTTCTGAAT | ATATAGATAC | GACCAATGCA | ACCACTTCAA | ATTTGAACG | CCCGATCTTA | 1020 |
| TTTTTTTTGA | GGAAGGTATA | TGATAAAACT | CCGATCTAGC | CCAACCACAT | GCTATAATCT | 1080 |
| TGTACCATAT | GAAACCACGT | CTGCTATTTT | GGCGGTTGCC | TCAAAACAAA | AGTAATGTTA | 1140 |
| TCCGGTTTCC | AACTCAAAGA | AAGAGAGTCA | GGTAGCGTGA | AGCTCCGAGG | CTGAGATGGG | 1200 |
| GACGAGCATG | GCGCCCCTAG | AGAGACCTCG | CCGTAGACGG | GGACATTGCG | GTTGACACGA | 1260 |
| GAGAAGTGAG | GGGGTTGCGA | GATGCGTGAG | ACAACACGTT | AGCAAAGTAG | GGAGAGGGTA | 1320 |
| GAAGAACTAA | GGGAGAAAGA | AGAGCAGTAG | CCGGCGAAAC | ATTGTACACC | ATTTTTTTC | 1380 |
| CAGCGACCTA | GCGAATAGGC | AGGCCCTACA | AAATCTCGTT | TGGTTTTCCC | ACGCCGACAA | 1440 |
| GCTCCAACCA | GCCATACCAT | ACCATAGGCG | TCTCACATGT | CCTTCTAGTC | TTCGCAAAAA | 1500 |
| GTAATTATTT | TTGCCGGACA | ATGCAAGGAG | TGATATTTTT | ATATAGTTTT | CCTTCCTTTT | 1560 |
| TTTTGCGAAT | ACTATAGTTT | TCCTTCTTTA | GAAAAGCAG | TCCTTCCATA | GTTTCTTTTG | 1620 |
| TGAAAGCAAT | GCCTTTTTAG | CGATTGGGAT | GTTCCTTTTT | AGAGCAAAAA | AAAACATCTT | 1680 |
| ACACTTTTTG | GCAAAACCGA | CGACGAAGGC | TGGAAAAAG | AAGTGACGAA | GGCTGAAAGT | 1740 |
| GGCGAGACAC | GTGAGGGCCC | ATGGCTTCCG | TCCGGCCCAG | CGGCGCACGA | CCCCGGCCCG | 1800 |
| CCCGGGCCCA | CAGATCCGCT | TCTCCCTCGC | CCCCGTTTCC | CCCTCCCTCC | CTCTCGTTGC | 1860 |
| TTCCACTCCA | CTGTTCTCCT | CCCCTGTCCA | AAGCGGCCAC | GGACCGGAAA | AAATCACGGC | 1920 |
| TTTCCGTTGC | GTCTCCGGCG | CCACACTCCT | CCTCCTCCTC | CCTCCGGCCG | CTATAAAGCG | 1980 |
| CGCCGGGCCA | CGGGCCCCGC | GGACAATGGG | ATCCCGTCC | GCCGCCATCG | ACGAAGATGC | 2040 |
| TCTGCCTCAC | CGCCTCCTCC | TCGCCCTCGC | CCTCGCCCTC | TCTCCGCCG | CGCCCCTCCC | 2100 |
| GTCCCGCTGC | TGACCGGCCC | GGACCGGGGA | TCTCGGTGAG | TCACTCGGGA | TCTTCATTTC | 2160 |
| TTTTCTTTTC | TTTCGTTTCC | GGCCTCCGTT | CTGCCAGCCG | GAGGTTCCCT | GATGCGATGC | 2220 |
| CGCGCGCGCA | GGGCGGCGGC | AATGTGCGGC | TGA | | | 2253 |

(2) INFORMATION FOR SEQ ID NO:13:

(i) SEQUENCE CHARACTERISTICS:
  (A) LENGTH: 1045 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Triticum aestivum
  (B) STRAIN: Biggar (xi) SEQUENCE DESCRIPTION: SEQ ID NO:13:

| | | | | | | |
|---|---|---|---|---|---|---|
| CCATGGCTTC | CGTCCGGCCC | AGCGGCGCAC | GACCCCGGCC | CGCCCGGGCC | CACAGATCCG | 60 |
| CTTCTCCCTC | GCCCCCGTTT | CCCCCTCCCT | CCCTCTCGTT | GCTTCCACTC | CACTGTTCTC | 120 |

-continued

| | | | | | | |
|---|---|---|---|---|---|---|
|CTCCCCTGTC|CAAAGCGGCC|ACGGACCGGA|AAAAATCACG|GCTTTCCGTT|GCGTCTCCGG|180|
|CGCCACACTC|CTCCTCCTCC|TCCCTCCGGC|CGCTATAAAG|CGCGCCGGGC|CACGGGCCCC|240|
|GCGGACAATG|GGATCCCCGT|CCGCCGCCAT|CGACGAAGAT|GCTCTGCCTC|ACCGCCTCCT|300|
|CCTCGCCCTC|GCCCTCGCCC|TCTCTCCCGC|CGCGCCCCTC|CCGTCCCGCT|GCTGACCGGC|360|
|CCGGACCGGG|GATCTCGGTG|AGTCACTCGG|GATCTTCATT|TCTTTTCTTT|TCTTTCGTTT|420|
|CCGGCCTCCG|TTCTGCCAGC|CGGAGGTTCC|CTGATGCGAT|GCCGCGCGCG|CAGGGCGGCG|480|
|GCAATGTGCG|GCTGAGCGCG|GTGCCCGCGC|CGTCTTCGCT|TCGCTGGTCG|TGGCCGCGGA|540|
|AGGTGAGCCC|TCTCCCCTGT|CTACCCAGAT|TTGCGACCCT|GATCCCTGT|TGTCGCCGGG|600|
|CAAACTGAAT|CTGATCCACG|CTGGTTATTG|GAAATACTGT|AGTATATATA|CTACTAATAA|660|
|ACCTGAGGCT|GGGATTCGTC|CACCTGACGC|CGTCCACTGA|GGAACAAGTG|GATGCGATTT|720|
|CGATTGAATT|TCTCTGCCTT|TACGCGATCC|GTACGCACAA|TATCCCCTCC|TGCGGTATCT|780|
|CAACCGTATT|ACTTTCTGCA|CAACCCAAAT|GCGTATAATC|TTTGCTGAAT|CTATCAACCA|840|
|ATAATCTGTG|ATGAATATAT|CAACCAAATT|AGTTGCTGCA|TTGTGACAAA|TATATTTAAT|900|
|TGATATAGGC|AAATGTTCAT|GTGCTGTATC|TCCATTACTT|CTTTAGTTGT|TGTAAATCTG|960|
|CCGCTCGCTC|TAACTGTCGT|TCATTTTGG|AAGGCCAAGA|GCAAGTTCTC|TGTTCCCGTG|1020|
|TCTGCGCCAA|GAGACTACAC|CATGG| | | |1045|

( 2 ) INFORMATION FOR SEQ ID NO:14:

( i ) SEQUENCE CHARACTERISTICS:
        ( A ) LENGTH: 1086 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Triticum aestivum
        ( B ) STRAIN: Biggar ( x i ) SEQUENCE DESCRIPTION: SEQ ID NO:14:

| | | | | | | |
|---|---|---|---|---|---|---|
|AGACGGGGAC|ATTGCGGTTG|ACACGAGAGA|AGTGAGGGGG|TTGCGAGATG|CGTGAGACAA|60|
|CACGTTAGCA|AAGTAGGGAG|AGGGTAGAAG|AACTAAGGGA|GAAAGAAGAG|CAGTAGCCGG|120|
|CGAAACATTG|TACACCATTT|TTTTCCAGC|GACCTAGCGA|ATAGGCAGGC|CCTACAAAAT|180|
|CTCGTTTGGT|TTTCCCACGC|CGACAAGCTC|CAACCAGCCA|TACCATACCA|TAGGCGTCTC|240|
|ACATGTCCTT|CTAGTCTTCG|CAAAAAGTAA|TTATTTTTGC|CGGACAATGC|AAGGAGTGAT|300|
|ATTTTTATAT|AGTTTTCCTT|CCTTTTTTTT|GCGAATACTA|TAGTTTTCCT|TCTTTAGAAA|360|
|AAGCAGTCCT|TCCATAGTTT|CTTTTGTGAA|AGCAATGCCT|TTTTAGCGAT|TGGGATGTTC|420|
|CTTTTTAGAG|CAAAAAAAAA|CATCTTACAC|TTTTTGGCAA|AACCGACGAC|GAAGGCTGGA|480|
|AAAAGAAGT|GACGAAGGCT|GAAAGTGGCG|AGACACGTGA|GGGCCCATGG|CTTCCGTCCG|540|
|GCCCAGCGGC|GCACGACCCC|GGCCCGCCCG|GGCCCACAGA|TCCGCTTCTC|CCTCGCCCCC|600|
|GTTTCCCCCT|CCCTCCCTCT|CGTTGCTTCC|ACTCCACTGT|TCTCCTCCCC|TGTCCAAAGC|660|
|GGCCACGGAC|CGGAAAAAAT|CACGGCTTTC|CGTTGCGTCT|CCGGCGCCAC|ACTCCTCCTC|720|
|CTCCTCCCTC|CGGCCGCTAT|AAAGCGCGCC|GGGCCACGGG|CCCCGCGGAC|AATGGGATCC|780|

| | | | | | |
|---|---|---|---|---|---|
| CCGTCCGCCG | CCATCGACGA | AGATGCTCTG | CCTCACCGCC | TCCTCCTCGC | CCTCGCCCTC | 840
| GCCCTCTCTC | CCGCCGCGCC | CCTCCCGTCC | CGCTGCTGAC | CGGCCCGGAC | CGGGGATCTC | 900
| GGTGAGTCAC | TCGGGATCTT | CATTTCTTTT | CTTTTCTTTC | GTTTCCGGCC | TCCGTTCTGC | 960
| CAGCCGGAGG | TTCCCTGATG | CGATGCCGCG | CGCGCAGGGC | GGCGGCAATG | TGCGGCTGAG | 1020
| CGCGGTGCCC | GCGCCGTCTT | CGCTTCGCTG | GTCGTGGCCG | CGGAAGGTGA | GCCCTCTCCC | 1080
| CTGTCT | | | | | | 1086

(2) INFORMATION FOR SEQ ID NO:15:

(i) SEQUENCE CHARACTERISTICS:
        (A) LENGTH: 682 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Triticum aestivum
        (B) STRAIN: Biggar (xi) SEQUENCE DESCRIPTION: SEQ ID NO:15:

| | | | | | |
|---|---|---|---|---|---|
| GACCGGGGAT | CTCGGTGAGT | CACTCGGGAT | CTTCATTTCT | TTTCTTTTCT | TTCGTTTCCG | 60
| GCCTCCGTTC | TGCCAGCCGG | AGGTTCCCTG | ATGCGATGCC | GCGCGCGCAG | GGCGGCGGCA | 120
| ATGTGCGGCT | GAGCGCGGTG | CCCGCGCCGT | CTTCGCTTCG | CTGGTCGTGG | CCGCGGAAGG | 180
| TGAGCCCTCT | CCCCTGTCTA | CCCAGATTTG | CGACCCTGAT | CCCCTGTTGT | CGCCGGGCAA | 240
| ACTGAATCTG | ATCCACGCTG | GTTATTGGAA | ATACTGTAGT | ATATATACTA | CTAATAAACC | 300
| TGAGGCTGGG | ATTCGTCCAC | CTGACGCCGT | CCACTGAGGA | ACAAGTGGAT | GCGATTTCGA | 360
| TTGAATTTCT | CTGCCTTTAC | GCGATCCGTA | CGCACAATAT | CCCCTCCTGC | GGTATCTCAA | 420
| CCGTATTACT | TTCTGCACAA | CCCAAATGCG | TATAATCTTT | GCTGAATCTA | TCAACCAATA | 480
| ATCTGTGATG | AATATATCAA | CCAAATTAGT | TGCTGCATTG | TGACAAATAT | ATTTAATTGA | 540
| TATAGGCAAA | TGTTCATGTG | CTGTATCTCC | ATTACTTCTT | TAGTTGTTGT | AAATCTGCCG | 600
| CTCGCTCTAA | CTGTCGTTCA | TTTTTGGAAG | GCCAAGAGCA | AGTTCTCTGT | TCCCGTGTCT | 660
| GCGCCAAGAG | ACTACACCAT | GG | | | | 682

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:16:

| | | |
|---|---|---|
| ACAATGGGAT | CCGACCATGG | TCCGT | 25

(2) INFORMATION FOR SEQ ID NO:17:

(i) SEQUENCE CHARACTERISTICS:
        (A) LENGTH: 24 base pairs
        (B) TYPE: nucleic acid (C) STRANDEDNESS: single
(D) TOPOLOGY: linear (i i) MOLECULE TYPE: DNA (genomic)

(i i i) HYPOTHETICAL: NO (x i) SEQUENCE DESCRIPTION: SEQ ID NO:17:

GTGCGGCTGA CGACCATGGT CCGT 24

(2) INFORMATION FOR SEQ ID NO:18:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (x i) SEQUENCE DESCRIPTION: SEQ ID NO:18:

TACACCATGG TCCGTCCTGT A 21

(2) INFORMATION FOR SEQ ID NO:19:

(i) SEQUENCE CHARACTERISTICS:
(A) LENGTH: 240 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (v i) ORIGINAL SOURCE:
(A) ORGANISM: Triticum aestivum
(B) STRAIN: Biggar (x i) SEQUENCE DESCRIPTION: SEQ ID NO:19:

CCCGTCCGCC GCCATCGACG AAGATGCTCT GCCTCACCGC CTCCTCCTCG CCCTCGCCCT 60

CGCCCTCTCT CCCGCCGCGC CCCTCCCGTC CCGCTGCTGA CCGGCCCGGA CCGGGGATCT 120

CGGTGAGTCA CTCGGGATCT TCATTTCTTT TCTTTTCTTT CGTTTCCGGC CTCCGTTCTG 180

CCAGCCGGAG GTTCCCTGAT GCGATGCCGC GCGCGCAGGG CGGCGGCAAT GTGCGGCTGA 240

(2) INFORMATION FOR SEQ ID NO:20:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (x i) SEQUENCE DESCRIPTION: SEQ ID NO:20:

CTCTGCCTTT ACGCGATCC 19

(2) INFORMATION FOR SEQ ID NO:21:

(i) SEQUENCE CHARACTERISTICS:
(A) LENGTH: 19 base pairs
(B) TYPE: nucleic acid

```
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:21:

CGCGATCCAG ACTGAATGC                                                              19

( 2 ) INFORMATION FOR SEQ ID NO:22:

( i ) SEQUENCE CHARACTERISTICS:
        ( A ) LENGTH: 82 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Triticum aestivum
        ( B ) STRAIN: Biggar ( x i ) SEQUENCE DESCRIPTION: SEQ ID NO:22:

Met  Arg  Phe  Arg  Leu  Asn  Phe  Ser  Ala  Phe  Thr  Arg  Ser  Ala  Lys  Ser
1                   5                        10                      15

Lys  Phe  Ser  Val  Pro  Val  Ser  Ala  Pro  Arg  Asp  Tyr  Thr  Met  Ala  Thr
               20                       25                      30

Ala  Glu  Asp  Gly  Phe  Gly  Asp  Leu  Pro  Ile  Tyr  Asp  Leu  Asp  Pro  Lys
          35                       40                      45

Phe  Ala  Gly  Phe  Lys  Asp  His  Phe  Ser  Tyr  Arg  Met  Lys  Lys  Tyr  Leu
     50                       55                      60

Glu  Gln  Lys  His  Ser  Ile  Glu  Lys  Tyr  Glu  Gly  Gly  Leu  Glu  Glu  Phe
65                        70                      75                      80

Ser  Lys
```

REFERENCES

1. Ausubel, F. A., Brent, R., Kingston, R. E., Moore, D. D., Seidman, J. G., Smith, J. A. and Struhl. K. (eds.). (1994). Current Protocols in Molecular Biology. John Wiley & Sons, New York.
2. Baba, T., Kimura, K., Mizuno, K., Etoh, H., Ishida, Y., Shida, O. and Arai, Y. (1991). Sequence conservation of the catalytic regions of amylolytic enzymes in maize branching enzyme-I. Biochem. Biophys. Res. Commun. 181: 87–94.
3. Båga M., Chibbar R. N. and Kartha K. K. (1995). Molecular cloning and expression analysis of peroxidase genes from wheat. Plant Mol. Biol.29:647–662.
4. Barcelo P., Hagel C., Becker D., Martin A. and Lörz H. (1994). Transgenic cereal (tritordeum) plants obtained at high efficiency by microprojectile bombardment of inflorescence tissue. Plant J. 5:583–592.
5. Becker D., Brettschneider R. and Lörz H. (1994). Fertile transgenic wheat from microprojectile bombardment of scutellar tissue. Plant J. 5:299–307.
6. Bradford, M. M. (1976). A rapid and sensitive method for quantitation of microgram quantities of protein using the principle of protein-dye binding. Anal. Biochem. 72:248–254.
7. Callis J., Fromm M. and Walbot V. (1987). Introns increase gene expression in cultured maize cells. Genes Devel. 1:1183–1200.
8. Castillo A. M., Vasil V. and Vasil I. K. (1994). Rapid production of fertile transgenic plants of rye (Secale cereale L.). Bio/Technology 12:1366–1371.
9. Chibbar R. N., Kartha K. K., Datla R. S. S., Leung N., Caswell K., Mallard C. S. and Steinhauer L. (1993). The effect of different promoter-sequences on transient expression of gus reporter gene in cultured barley (Hordeum vulgare L.) cells. Plant Cell Rep. 12:506–509.
10. Cristou P., Ford T. L. and Kofron M. (1991). Production of transgenic rice (Oryza sativa L.) plants from agronomically important indica and japonica varieties via electric discharge particle acceleration of exogenous DNA into immature zygotic embryos. Bio/Technology 9:957–962.
11. Datla, R. S. S., Hammerlindl, J. K., Pelcher, L. E., Crosby, W. L. and Selvaraj, G. (1991). A bifunctional fusion between β-glucuronidase and neomycin phosphotransferase: a broad-spectrum marker enzyme for plants. Gene 101:239–246.
12. Datta S. K., Peterhans A., Datta K. and Potrykus I. (1990). Genetically engineered fertile indica-rice recovered from protoplasts. Bio/Technology 8:736–740.

13. D'Halluin K., Bonne E., Bossut M., De Beuckeleer M. and Leemans J. (1992). Transgenic maize plants by tissue electroporation. Plant Cell 4:1495–1505.
14. Doyle, J. J. and Doyle, J. L. (1990). Isolation of plant DNA from fresh tissue. Focus 12:13–15.
15. Fromm M. E., Morrish F., Armstrong C., Williams R., Thomas J. and Klein T. M. (1990). Inheritance and expression of chimeric genes in the progeny of transgenic maize plants. Bio/Technology 8:833–839.
16. Gamborg, O. L., Miller, R. A. and Ojima, K. (1968). Nutrient requirements of suspension cultures of soybean root cells. Exp. Cell Res. 50:151–158.
17. Goodall G. J. and Filipowicz W. (1991) Different effects of intron nucleotide composition and secondary structure on pre-mRNA splicing in monocot and dicot plants. EMBO J. 10:2635–2644.
18. Gordon-Kamm W. J., Spencer T. M., Mangano M. L., Adams T. R., Daines R. J., Start W. G., O'Brien J. V., Chambers S. A., Adams W. R., Willetts N. G., Rice T. B. , Mackey C. J., Krueger R. W., Kausch A. P. and Lemaux P. G. (1990). Transformation of maize cells and regeneration of fertile transgenic plants. Plant Cell 2:603–618.
19. Hanahan, D. (1983). Studies on transformation of *Escherichia coli* with plasmids. J. Mol. Biol. 166:557–580.
20. Hayakawa T., Zhu Y., Itoh K., Kimura Y., Izawa T., Shimamoto K. and Toriyama S. (1992). Genetically engineered rice resistant to rice stripe virus, an insect-transmitted virus. Proc Natl Acad Sci USA 89:9865–9869.
21. Inoue, H., Nojima, H. and Okayama, H. (1990). High efficiency transformation of *Escherichia coli* with plasmids. Gene 96:23–28.
22. Jefferson, R. A., Kavanagh, T. A. and Bevan, M. W. (1987). GUS fusions: β-glucuronidase as a sensitive and versatile gene fusion marker in higher plants. EMBO J. 6:3901–3907.
23. Kawasaki, E. S. (1990). Sample preparation from blood, cells, and other fluids. In: Innis, M. A., Gelfand, D. H., Sninsky, J. J., White, T. J. (eds.). PCR Protocols: A Guide to Methods and Applications, pp. 146–152. Academic Press, San Diego.
24. Kawasaki, T., Mizuno, K., Baba, T. and Shimada, H. (1993). Molecular analysis of the gene encoding a rice starch branching enzyme. Mol. Gen. Genet. 237:10–16.
25. Keith, B. and Chua, N.-H. (1986). Monocot and dicot pre-mRNAs are processed with different efficiencies in transgenic tobacco. EMBO J. 5:2419–2425.
26. King, P. V. and Blakesley, R. W. (1986). Optimizing DNA ligations for transformation. FOCUS 8:1–3.
27. Li L., Qu R., de Kochko A., Fauquet C. and Beachy R. N. (1993). An improved rice transformation system using the biolistic method. Plant Cell Rep. 12:250–255.
28. Logemann, J., Schell, J. and Willmitzer, L. (1987). Improved method for the isolation of RNA from plant tissues. Anal. Biochem. 163:16–20.
29. Maas C., Laufs J., Grant S., Korfhage C. and Werr W. (1991). The combination of a novel stimulatory element in the first exon of the maize Shrunken-1 gene with the following intron 1 enhances reporter gene expression up to 1000-fold. Plant Mol. Biol. 16:199–207.
30. Marchuk, D., Drumm, M., Saulino, A., Collins, F. S. (1991). Construction of T-vectors, a rapid and general system for direct cloning of unmodified PCR products. Nucl. Acids Res. 19:1154.
31. McElroy, D., Zhang, W., Cao, J. and Wu, R. (1990). Isolation of an efficient actin promoter for use in rice transformation. Plant Cell 2:163–171.
32. Murashige, T. and Skoog, F. (1962). A revised medium for rapid growth and bioassays with tobacco tissue cultures. Physiol. Plant. 15:473–497.
33. Nakamura, Y. and Yamanouchi, H. (1992). Nucleotide sequence of a cDNA encoding starch-branching enzyme, or Q-enzyme I, from rice endosperm. Plant Physiol. 99: 1265–1266.
34. Nehra N. S., Chibbar R. N. and Kartha K. K. (1995). Wheat transformation: Methods and Prospects. Plant Breeding Abstracts (CAB) 65(6):803–808, 1995.
35. Nehra, N. S., Chibbar, R. N., Leung, N., Caswell, K., Mallard, C., Steinhauer, L., Baga, M. and Kartha, K. K. (1994). Self-fertile transgenic wheat plants regenerated from isolated scutellar tissues following microprojectile bombardment with two distinct gene constucts. Plant J. 5:285–297.
36. Rhodes C. A., Pierce D. A., Mettler I. J., Mascarenhas D. and Detmer J. J. (1988). Genetically transformed maize plants from protoplasts. Science 240:204–207.
37. Ritala A., Aspegren K., Kurten U., Salmenkallio-Marttila M., Mannonen L., Hannus R., Kauppinen V., Teeri T. H. and Enari T.-M. (1994). Fertile transgenic barley by particle bombardment of immature embryos. Plant Mol. Biol. 24:317–325.
38. Sambrook, J., Fritsch E. F. and Maniatis, T. (eds.) (1989). Molecular Cloning: A Laboratory Manual, Cold Spring Harbor Laboratory Press, Cold Spring Harbor, N.Y.
39. Sanford, J. C., Smith, F. D. and Russel, J. A. (1993). Optimizing the biolistic process for different biological applications. Meth. Enzymol. 217:483–509.
40. Shimamoto K., Terada R., Izawa T. and Fujimoto H. (1989). Fertile transgenic rice plants regenerated from transformed protoplasts. Nature 338:274–276.
41. Somers D. A., Rines H. W., Gu W., Kaeppler H. F. and Bushnell W. R. (1992). Fertile, transgenic oat plants. Bio/Technology 10:1589–1594.
42. Toki S., Takamatsu S., Nojiri C., Ooba S., Anzai H., Iwata M., Christensen A. H., Quail P. H. and Uchimiya H. (1992). Expression of a maize ubiquitin gene promoter-bar chimeric gene in transgenic rice plants. Plant Physiol. 100:1503–1507.
43. Vasil V., Clancy M., Ferl R. J., Vasil I. K. and Hannah L. C. (1989). Increased gene expression by the first intron of maize Shrunken-1 locus in grass species. Plant Physiol. 91:1575–1579.
44. Vasil V., Castillo A. M., Fromm M. E. and Vasil I. K. (1992). Herbicide resistant fertile transgenic wheat plants obtained by microprojectile bombardment of regenerable embryogenic callus. Bio/Technology 10:667–574.
45. Vasil V., Srivastava V., Castillo A. M., Fromm M. E. and Vasil I. K. (1993). Rapid production of transgenic wheat plants by direct bombardment of cultured immature embryos. Bio/Technology 11:1553–1558.
46. Wan Y. and Lemaux P. G. (1994). Generation of large numbers of independently transformed fertile barley plants. Plant Physiol. 104:37–48.
47. Weeks J. T., Anderson O. D. and Blechl A. E. (1993). Rapid production of multiple independent lines of fertile transgenic wheat (*Triticum aestivum*) . Plant Physiol. 102: 1077–1084.
48. Xu X. and Li B. (1994). Fertile transgenic Indica rice plants obtained by electroporation of the seed embryo cells. Plant Cell Rep. 13:237–242.

What we claim is:

1. A DNA fragment for directing the expression of foreign or endogenous genes in cells of monocot plants, said fragment comprising the sequence of a part of a type I starch branching enzyme gene (wbeI) present in wheat, which part is a 3'-region downstream commencing at an ATG start codon for translation of said gene, and a 5'-region upstream of said ATG start codon, or a part of said sequence, said sequence or said part thereof being effective to cause expression of said foreign or endogenous gene in said cells at a level higher than is possible in the absence of said sequence or part thereof, wherein said DNA fragment is a sequence derived from a plasmid pBE64:8-2.

2. A DNA fragment according to claim 1 comprising at least one of two promoter regions, P1 and P2, a first of said promoters P1 being positioned upstream of said ATG start codon and a second of said promoters P2 being positioned downstream of said start codon.

3. A DNA fragment according to claim 1 wherein said starch branching enzyme gene comprises first and second introns and said DNA sequence includes first and second promoter regions P1 and P2, one promoter region P1 being located in said 5' upstream region and the other promoter region P2 being located in said second intron.

4. A DNA fragment for directing the expression of foreign or endogenous genes in cells of monocot plants, said fragment comprising the sequence of a part of a type I starch branching enzyme gene (wbeI) present in wheat, which part is a 3'-region downstream commencing at an ATG start codon for translation of said gene, and a 5'-region upstream of said ATG start codon, or a part of said sequence, said sequence or said part thereof being effective to cause expression of said foreign or endogenous gene in said cells at a level higher than is possible in the absence of said sequence or part thereof, said DNA fragment having a swquence comprising at least a part of SEQ ID NO:1.

5. A DNA fragment according to claim 4 comprising at least SEQ ID NO:4.

6. A DNA fragment according to claim 4 comprising at least SEQ ID NO:12.

7. A DNA fragment according to claim 4 comprising at least SEQ ID NO:3.

8. A DNA fragment according to claim 4 comprising SEQ ID NO:5.

9. A DNA fragment according to claim 4 comprising SEQ ID NO:6.

10. A construct comprising a DNA fragment linked to a gene other than wbeI, said fragment being the sequence of a part of a type I starch branching enzyme gene (wbeI) present in wheat, which part is a 3'-region downstream commencing at an ATG start codon for translation of said gene, and a 5'-region upstream of said ATG start codon, or a part of said sequence, said sequence or said part thereof being effective to cause expression of said foreign or endogenous gene in said cells at a level higher than is possible in the absence of said sequence or part thereof, wherein said DNA fragment has a sequence comprising at least a part of SEQ ID NO:1.

11. A construct according to claim 10 further comprising a polyadenylation sequence transcriptionally fuse to said gene.

12. A construct according to claim 10 further comprising a selectable marker gene that is under the control of a constitutive promoter.

13. A vector for introducing a foreign or endogenous gene into a genome of a monocot plant, comprising a DNA fragment comprising a part of a type I starch branching enzyme gene (wbeI) present in wheat, which part is a 3'-region downstream commencing at an ATG start codon for translation of said gene, and a 5'-region upstream of said ATG start codon, or a part of said sequence, said sequence or said part thereof being effective to cause expression of said foreign or endogenous gene in said cells at a level higher than is possible in the absence of said sequence or part thereof, and wherein said DNA fragment has a sequence comprising at least a part of SEQ ID NO:1.

14. A vector according to claim 13 further comprising a foreign or endogenous gene and a polyadenylation sequence transcriptionally fused to said foreign or endogenous gene.

15. A vector according to claim 13 further encoding a gene encoding a selectable marker under the control of a constitutive promoter.

16. The vector designated pGK101.

17. The vector designated pGK102.

18. The vector designated pGK105.

19. The vector designated pGK107.

20. A plant cell having a genome containing a foreign gene or an endogenous gene other than wbeI under expression control of a promoter, said promoter including a DNA sequence comprising a part of a 3'-region of wbeI gene present in wheat commencing at an ATG start codon for translation of said wbeI gene and a 5'-region upstream of said ATG start codon, wherein said sequence comprises at least a part of SEQ ID NO:1.

21. A transgenic plant containing a foreign gene or an endogenous gene other than wbeI, under expression control of a promoter, said promoter including a DNA sequence comprising a part of a 3'-region of wbeI present in wheat commencing at an ATG start codon for translation of said wbeI gene and a 5'-region upstream of said ATG start codon, wherein said sequence comprises at least a part of SEQ ID NO:1.

22. A method of producing transgenic monocot plants, which comprises introducing a vector comprising a foreign or endogenous gene and a DNA sequence of a part of a type I starch branching enzyme gene (wbeI) present in wheat, which part is a 3'-region downstream commencing at an ATG start condon for translation of said gene and a 5'-region upstream of said ATG start codon, or a part of said sequence, said sequence or said part thereof being effective to cause expression of said foreign or endogenous gene at a level higher than is possible in the absence of said sequence or part thereof, into a totipotent explant of a monocot plant to form a transformed explant, and culturing the transformed explant to form a mature transgenic monocot plant, wherein said sequence comprises at least a part of SEQ ID NO:1.

23. A method according to claim 22, wherein said totipotent explant is a zygotic embryo from which the embryo axis has been detached.

24. An isolated, genetically transformed totipotent explant of a monocot plant comprising a foreign or endogenous gene and a DNA sequence of a part of a type I starch branching enzyme (wbeI) present in wheat, which part is a 3'-region downstream commencing at an ATG start codon for translation of said gene, and a 5'-region upstream of said ATG start codon, or a part of said sequence, said sequence or said part thereof being effective to cause expression of said foreign or endogenous gene in plants developed from said explant at a level higher than is possible in the absence of said sequence or part thereof, said totipotent explant being a zygotic embryo from which the embryo axis has been detached, and wherein said sequence comprises at least a part of SEQ ID NO:1.

* * * * *